(12) United States Patent
Takayama et al.

(10) Patent No.: US 12,050,215 B2
(45) Date of Patent: Jul. 30, 2024

(54) MACROMOLECULAR STRUCTURES AND USES THEREOF

(71) Applicant: The Regents of the University of Michigan, Ann Arbor, MI (US)

(72) Inventors: Shuichi Takayama, Ann Arbor, MI (US); Cameron Louttit, Ann Arbor, MI (US); James J. Moon, Ann Arbor, MI (US); Taisuke Kojima, Ann Arbor, MI (US); Priyan Weerappuli, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 422 days.

(21) Appl. No.: 15/776,346

(22) PCT Filed: Nov. 16, 2016

(86) PCT No.: PCT/US2016/062250
§ 371 (c)(1),
(2) Date: May 15, 2018

(87) PCT Pub. No.: WO2017/087505
PCT Pub. Date: May 26, 2017

(65) Prior Publication Data
US 2020/0200741 A1 Jun. 25, 2020

Related U.S. Application Data

(60) Provisional application No. 62/256,321, filed on Nov. 17, 2015.

(51) Int. Cl.
*G01N 33/544* (2006.01)
*A01N 25/10* (2006.01)
*A01N 57/16* (2006.01)
*C12N 11/089* (2020.01)

(52) U.S. Cl.
CPC ........... *G01N 33/544* (2013.01); *A01N 25/10* (2013.01); *A01N 57/16* (2013.01); *C12N 11/089* (2020.01); *G01N 2500/04* (2013.01)

(58) Field of Classification Search
CPC .. G01N 33/544; G01N 2500/04; A01N 25/10; A01N 57/16
See application file for complete search history.

(56) References Cited

U.S. PATENT DOCUMENTS

| | | | | |
|---|---|---|---|---|
| 4,525,457 | A * | 6/1985 | Sakata et al. | 435/178 |
| 5,440,025 | A * | 8/1995 | Marx et al. | 536/25.4 |
| 10,047,345 | B2 * | 8/2018 | Peled et al. | C12N 5/0667 |
| 2005/0220882 | A1 * | 10/2005 | Pritchard | A61F 9/00772 |
| | | | | 424/618 |
| 2007/0110813 | A1 | 5/2007 | Ingenito et al. | |
| 2008/0003142 | A1 * | 1/2008 | Link | G01N 15/147 |
| | | | | 264/219 |
| 2008/0234183 | A1 * | 9/2008 | Hallbrink et al. | 514/12 |
| 2009/0136932 | A1 * | 5/2009 | Craighead | D01D 5/0007 |
| | | | | 536/25.4 |
| 2013/0017177 | A1 * | 1/2013 | Da Silva Correia | A61L 27/28 |
| | | | | 522/89 |
| 2014/0038894 | A1 | 2/2014 | Corrigan et al. | |

FOREIGN PATENT DOCUMENTS

| | | | |
|---|---|---|---|
| WO | 2004-018066 | 3/2004 | |
| WO | WO-2007136717 A1 * | 11/2007 | ......... C12N 15/1006 |
| WO | 2015-034360 | 3/2015 | |

OTHER PUBLICATIONS

Arita et al. "Structural basis for histone N-terminal recognition by human peptidylarginine deiminase 4" PNAS Apr. 4, 2006, vol. 103, No. 14: 5291-5296 (Year: 2006).*
Jain et al. "Synthesis of Protein-Loaded Hydrogel Particles in an Aqueous Two-Phase System for Coincident Antigen and CpG Oligonucleotide Delivery to Antigen-Presenting Cells" Biomacromolecules 2005, 6, 2590-2600 (Year: 2005).*
Liao et al. "Controlled release from fibers of polyelectrolyte complexes" Journal of Controlled Release 104 (2005) 347-358 (Year: 2005).*
Rasenack et al. (2004) Micron-Size Drug Particles: Common and Novel Micronization Techniques, Pharmaceutical Development and Technology, 9:1, 1-13, DOI: 10.1081/PDT-120027417 (Year: 2004).*
Sugasawa et al. "Nonconservative segregation of parental nucleosomes during simian virus 40 chromosome replication in vitro" PNAS Feb. 1, 1992 89 (3) 1055-1059; https://doi.org/10.1073/pnas.89.3.1055 (Year: 1992).*
NCBI Reference Sequence NC_001669.1, 18 sheets downloaded Dec. 31, 2020 from https://www.ncbi.nlm.nih.gov/nuccore/NC_001669.1 (Year: 1984).*
Annunziato, A. (2008) DNA Packaging: Nucleosomes and Chromatin. Nature Education 1(1):26 on 5 sheets (Year: 2008).*
Baas et al. (1976) "Cleavage map of bacteriophage PhiX174 RF DNA by restriction enzymes" Nucl. Acids Res. 3(8):1947-1960 (Year: 1976).*
Nedjari ("Microstructuration of Nanofibrous membranes by electrospinning: Application to tissue engineering" University of Strasbourg, Doctoral School in Physics and Chemistry—ICPEES Institute of Chemistry for Energy and Environment and Health, published Oct. 21, 2014) (Year: 2014).*
Antipina, Maria N. et al. "Studies of nanoscale structural ordering in planar DNA complexes with amphiphilic mono- and polycations" Surface Science, 2003, vols. 532-535, pp. 1025-1033.

(Continued)

*Primary Examiner* — Nancy J Leith
*Assistant Examiner* — Jessica D Parisi
(74) *Attorney, Agent, or Firm* — Casimir Jones, S.C.; Tanya A. Arenson

(57) ABSTRACT

Provided herein are macromolecular structures comprising charged macromolecules. In particular, provided herein are synthetic neutrophil extracellular traps and uses thereof.

19 Claims, 17 Drawing Sheets

(56) References Cited

OTHER PUBLICATIONS

Beiter K, et al., An endonuclease allows *Streptococcus pneumoniae* to escape from neutrophil extracellular traps. Current Biology. Feb. 2006;16(4):401-407.
Brinkmann V, et al., Neutrophil Extracellular Traps: How to Generate and Visualize Them. Journal of Visualized Experiments. Feb. 24, 2010 [cited Jun. 2, 2015];(36), pp. 1-3.
Brinkmann V, et al., Neutrophil extracellular traps kill bacteria. Science. Mar. 5, 2004;303(5663):1532-1535.
Buchanan JT, et al., Dnase Expression Allows the Pathogen Group A *Streptococcus* to Escape Killing in Neutrophil Extracellular Traps. Current Biology. Feb. 2006;16(4):396-400.
Ge L, et al., Neutrophil extracellular traps in ischemia-reperfusion injury-induced myocardial no-reflow: therapeutic potential of Dnase-based reperfusion strategy. American Journal of Physiology—Heart and Circulatory Physiology. Mar. 1, 2015;308(5):H500-H509.
International Search Report and Written Opinion, International Patent Application No. PCT/US2016/062250 mailed Mar. 30, 2017.
Johns et al., Interactions Between Histone Fractions and DNA, Biochimica et Biophysical Acta 209 (1970) 54-57.
Klinman DM, et al., Therapeutic Potential of Oligonucleotides Expressing Immunosuppressive TTAGGG Motifs. Annals of the New York Academy of Sciences. Nov. 1, 2005;1058(1):87-95.
Kockritz-Blickwede M von, et al., Fetal calf serum contains heat-stable nucleases that degrade neutrophil extracellular traps. Blood. Dec. 10, 2009;114(25):5245-5246.
Lande, et al., Neutrophils activate plasmacytoid dentric cells by releasing self-DNA-peptide complexes in systemic lupus erythematosus. Science Translational Medicine. Mar. 9, 2011;3(73):73ra19-73ra19, 20 pages.
Macanovic M, et al., The Treatment of systemic lupus erythematosus (SLE) in NZB/W F1 hybrid mice; studies with recombinant murine Dnase and with dexamethasone. Clinical & Experimental Immunology. Nov. 1, 1996;106(2):243-252.
Neumann A, et al., Novel role of the antimicrobial peptide LL-37 in the protection of neutrophil extracellular trpas against degradation by bacterial nucleases. Journal of Innate Immunity. 2014;6(6):860-868.
Papadaki G, et al., Neutrophil extraceullar traps exacertabe Th1-mediated autoimmune responses in rheumatoid arthritis by promoting DC maturation. Eur J Immunol. Sep. 2, 2016, 46:2542-2554.
Shak S, et al., Recombinant human Dnase I reduces the viscosity of cystic fibrosis sputum. PNAS. Dec. 1, 1990;87 (23):9188-9192.
Sluyser et al., Interaction of Histones and Nucleic Acids In Vitro. Biochimica et Acta 199 (1970) 490-499.

\* cited by examiner

A

B

MACROMOLECULAR STRUCTURES AND USES THEREOF

This application is a 371 U.S. National Phase Entry of International Application No. PCT/US2016/062250, filed Nov. 16, 2016, which claims priority to U.S. provisional patent application No. 62/256,321, filed Nov. 17, 2015, each of which is herein incorporated by reference in their entireties.

STATEMENT REGARDING FEDERALLY SPONSORED RESEARCH OR DEVELOPMENT

This invention was made with government support under IIP1456281 awarded by the National Science Foundation and under CA196018 awarded by the National Institutes of Health. The Government has certain rights in the invention.

FIELD OF THE DISCLOSURE

Provided herein are macromolecular structures comprising charged macromolecules. In particular, provided herein are synthetic neutrophil extracellular traps and uses thereof.

BACKGROUND OF THE DISCLOSURE

Neutrophil extracellular traps (NETs) and associated structures produced by neutrophils and other cells such as macrophages are a recently-discovered mechanism of pathogen containment and killing wherein decondensed chromatin and granular proteins are combined and extruded into the extracellular space. These structures have been recognized as beneficial in the clearance of pathogens but deleterious as they are directly linked to a spectrum of pathologies including sepsis, systemic lupus erythematosus, rheumatoid arthritis, type 1 diabetes, cystic fibrosis, deep-vein thrombosis, preeclampsia, atherosclerosis, and cancer metastasis.

To date, all efforts to explore and manipulate these structures have required time-consuming, low-yield protocols using primary neutrophils or associated cells including some cell lines. Additionally, the structures produced are highly heterogeneous and difficult to study in a consistent, high-throughput manner.

Additional compositions and methods for use in studying NETs in vitro are needed.

SUMMARY OF THE DISCLOSURE

Provided herein are macromolecular structures comprising charged macromolecules. In particular, provided herein are synthetic neutrophil extracellular traps and uses thereof.

Early research into the interaction between DNA and histones focused upon the ability of histones to precipitate DNA but without regard for the structures formed (see e.g., Johns et al., Biochimica et Biophysical Acta 209 (1970) 54-57 and Sluyser et al., Biochimica et Acta 199 (1970) 490-499). The present disclosure provides methods for generating uniform three-dimensional structures that have nanoscale fibers that organize into well-defined micrometers to millimeters length scales. The resulting structures find use in a variety of research, screening, diagnostic tests, therapeutic, and industrial applications.

For example, in some embodiments, the present disclosure provides a composition comprising a plurality of uniformly shaped three-dimensional structures comprising a network of a polyanion (e.g., negatively charged polymer) and a polycation (e.g., positively charged polymer). The present disclosure is not limited to a particular polyanion. Examples include, but are not limited to, genomic DNA, mitochondrial DNA, bacterial DNA, viral DNA, synthetic DNA, oxidized DNA, oligonucleotides, synthetic RNA, miRNA, shRNA, siRNA, tRNA, mRNA, viral RNA, polystyrene sulfonate, polyglutamic acid, or hyaluronic acid, and combinations thereof. In some embodiments, the nucleic acid is between approximately 1 kilobase and 1 megabase in length (e.g., 1 kb, 10, kb, 50 kb, 100 kb, 500 kb, 1000 kb, etc.). The present disclosure is not limited to a particular polycation. Examples include, but are not limited to, histones, citrullinated histones, spermine, spermidine, polyimine, ethylamine, poly-L-lysine, poly-D-lysine, polyaniline, polypyrrole, polyvinylamine, or poly (diallyldimethylammonium chloride). In some embodiments, the final obtained structures have overall shapes that are spheres or discs with a diameter of 1 μm to 1 cm. In some embodiments, the internal structures comprise fibers, or bundles thereof, of the polyanion and the polycation. In some embodiments, the individual fibers, or bundles thereof, are approximately 7-500 nm (e.g., 7, 15, 30, 60, 120, 240, 480 nm) in diameter and 0.1-100 μm (e.g., 0.1, 10, 500 μm) in length. In some embodiments, the structures are in arrays. In some embodiments, the structures further comprise a test compound or therapeutic agent (e.g., a charged compound, a nucleic acid, a cytokine, or a protein).

Further embodiments provide a solid or semi-solid support comprising the structures described herein. The present disclosure is not limited to particular solid or semi-solid supports. Examples include, but are not limited to, a multiwell plate, a particle exterior, a well, a shell, a post, a hydrogel, an elastic surface, a curved surface, a cell, a tissue, a nucleic acid, or a microchannel.

In certain embodiments, the present disclosure provides a cell (e.g., bacterial cell or eukaryotic cell) or particle coated with a structure as described herein.

In yet other embodiments, the present disclosure provides a method or use of killing or inhibiting the growth of bacteria, comprising contacting the bacteria with a structure as described herein.

Additional embodiments provide a method of forming a plurality of uniformly shaped three-dimensional structures (e.g. sphere, cube, pyramid, rectangle, line, curve) comprising a network of a polyanion and a polycation, comprising: mixing a first polymer solution comprising a polyanion with a second polymer solution comprising a polycation such that the first and second polymer solutions form an aqueous two-phase system, wherein the structures form in the aqueous two-phase system. In some embodiments, the first polymer solution is dextran (DEX) and the second polymer solution is polyethylene glycol (PEG). In some embodiments, DEX is present in the aqueous two-phase system at a concentration of 5% to 30% (e.g., 5%, 10%, 15%, 20%, 25%, 30%). In some embodiments, the PEG is present in the aqueous two-phase system at a concentration of 5% to 80% (e.g., 5%, 10%, 15%, 20%, 25%, 30%, 40%, 50%, 60%, 70%, or 80%). In some embodiments, the first polymer solution is dehydrated and the first polymer solution is rehydrated by the second polymer solution.

In some embodiments, the present disclosure provides a method of forming a plurality of uniformly shaped three-dimensional structures comprising a network of a polyanion and a polycation, comprising: dehydrating a first solution comprising a polyanion and an excipient; and rehydrating said first solution with a second solution comprising a polycation such that the structures are formed. In some embodiments, the excipient is trehalose or dextran.

Further provided is a method of forming a plurality of uniformly shaped three-dimensional structures comprising a network of a polyanion and a polycation, comprising: introducing a first polymer solution comprising a polyanion through a first input channel of a microfluidic device and introducing a second polymer solution comprising a polycation solution through a second input channel of the microfluidic device such that the first and second polymer solutions mix and form said structures. In some embodiments, the first and second polymer solutions converge within a central mixing channel where the two solutions flow in parallel, allowing controlled mixing to occur at an interface.

In some embodiments, the present disclosure provides a plurality of uniformly shaped three-dimensional structures comprising a network of a polyanion and a polycation made by any of the aforementioned methods.

Yet other embodiments provide a system, comprising: any of the aforementioned compositions or structures; and a solid or semi-solid support. In some embodiments, the structures are affixed to the solid support.

Still other embodiments provide a method, comprising: a) contacting any of the aforementioned composition or structures with a test compound: and b) measuring a change in at least one property of the structure in the presence of the test compound relative to absence of the test compound. In some embodiments, the test compound is a drug. In some embodiments, the property is degradation of the structures.

Still other embodiments provide a method, comprising: a) contacting any of the aforementioned composition or structures with a test sample (e.g., a blood or blood product); and b) measuring binding of biomolecules in the test sample to the structures. In some embodiments, the biomolecule is an antibody.

Additional embodiments are described herein.

DEFINITIONS

Figure 1:
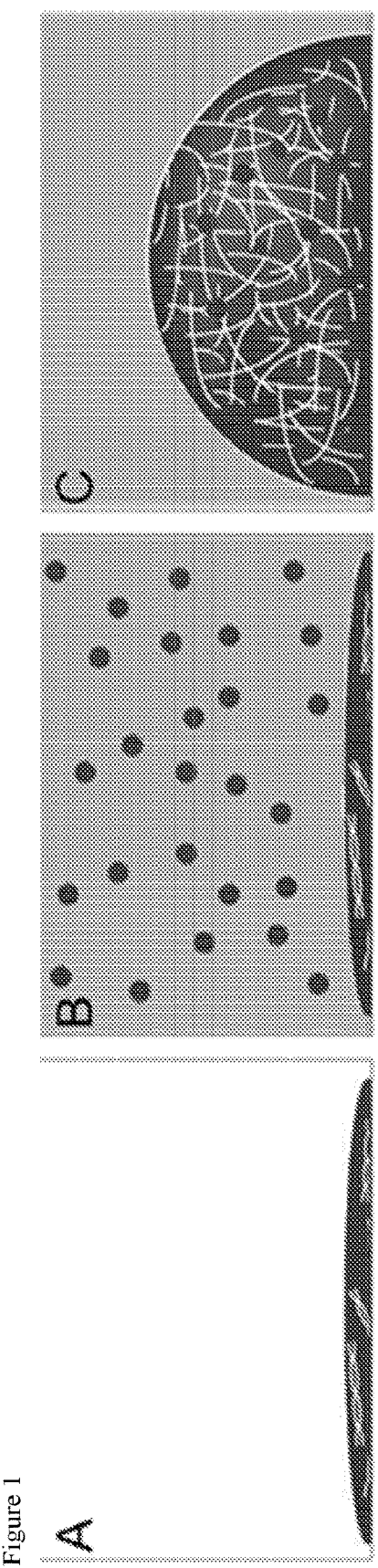
FIG. 1 shows rehydration of DNA-DEX spots with histone-PEG solution which spontaneously produces NET-like DNA-histone structures. (A) DNA-DEX droplets are pre-spotted and dehydrated in each well of a 96 well plate (A-C are side views). (B) Addition of PEG-histone solution to the well. (C) DNA-histone structures form via slow controlled diffusive mixing.

To facilitate an understanding of the present disclosure, a number of terms and phrases are defined below:

The term "sample" in the present specification and claims is used in its broadest sense. On the one hand it is meant to include a specimen or culture. On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present disclosure.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, antibodies, and the like that is a candidate for use to treat, prevent, or diagnose a disease, illness, sickness, or disorder of bodily function. Test compounds comprise both known and potential therapeutic and diagnostic compounds. A test compound can be determined to be therapeutic or diagnostic by screening using the screening methods of the present invention.

DETAILED DESCRIPTION OF THE DISCLOSURE

Provided herein are macromolecular structures comprising charged macromolecules. In particular, provided herein are synthetic neutrophil extracellular traps and uses thereof. For example, embodiments of the present disclosure provide uniformly shaped three-dimensional structures comprising a network of a polyanion and a polycation.

The structures described herein provide the advantage of having a uniform three dimensional macrostructure. The present disclosure is not limited to particular shapes of structures. In some embodiments, structures are formed as convex structures (e.g., resembling 'domes'), spheres or discs with a diameter of 1 µm to 1 cm (e.g., 100 µm-9 mm). In some embodiments, the size (e.g., diameter, area, or volume) of structures in a population (e.g., a population of structures produced in a single preparation) differ by no more than 30% (e.g., less than 25%, 20%, 15%, 10%, 5%, 4%, 3%, 2%, or 1% variation in size).

In some embodiments, the structures comprise fibers, and bundles thereof, of the polyanion and the polycation. In some embodiments, the individual fibers, or bundles thereof, are approximately 7-500 nm (e.g., 7, 15, 30, 60, 120, 240, 480 nm) in diameter and 0.1-100 µm (e.g., 0.1, 10, 500 µm) in length.

The present disclosure is not limited to a particular polyanion. Examples include, but are not limited to, genomic DNA, mitochondrial DNA, bacterial DNA, viral DNA, synthetic DNA, oligonucleotides, oxidized DNA, synthetic RNA, miRNA, shRNA, siRNA, tRNA, mRNA, viral RNA, polystyrene sulfonate, polyglutamic acid, or hyaluronic acid, and combinations thereof.

In some embodiments, the polyanion is a nucleic acid (e.g., those described herein). In some embodiments, the nucleic acid is between approximately 1 kilobase and 1 megabase in length (e.g., 1 kb, 10, kb, 50 kb, 100 kb, 500 kb, 1000 kb, etc.).

The present disclosure is not limited to a particular polycation. Examples include, but are not limited to, a histone, spermine, spermidine, polyimine, ethylamine, poly-L-lysine, poly-D-lysine, polyaniline, polypyrrole, polyvinylamine, or poly(diallyldimethylammonium chloride). In some embodiments, the structures are in arrays. In some embodiments, the structures further comprise a test compound or therapeutic agent (e.g., a charged compound, a nucleic acid, a cytokine, or a protein).

In some embodiments, structures are formed in an aqueous two phase system (ATPS) comprising a first polymer that comprises the polyanion (e.g., nucleic acid) and a second solution comprising a polymer comprising the polycation (e.g., histone). In some embodiments, the first polymer solution is DEX and the second polymer solution is PEG. In some embodiments, DEX is present in the aqueous two-phase system at a concentration of 5% to 30% (e.g., 5%, 10%, 15%, 20%, 25%, 30%). In some embodiments, the PEG is present in the aqueous two-phase system at a concentration of 5% to 80% (e.g., 5%, 10%, 15%, 20%, 25%, 30%, 40%, 50%, 60%, 70%, or 80%).

In some embodiments, structures are formed in the absence of an ATPS. For example, in some embodiments, structures are formed by dehydrating a first solution comprising a polyanion and an excipient; and rehydrating said first solution with a second solution comprising a polycation such that the structures are formed. In some embodiments, the excipient is trehalose or dextran.

The present disclosure is not limited to particular polymers. Any polymers that form an aqueous two phase system (ATPS) at a wide range of temperatures (See e.g., WO 2010/027590; herein incorporated by reference in its entirety) are suitable. Examples of suitable polymers include, but are not limited to, polyethylene glycol (PEG), dextran (DEX), and combinations of other polymers such as DEX-methylcellulose, DEX-polyvinyl alcohol, PEG-DEX sulfate, polyvinyl alcohol-DEX sulfate, hydroxypropyldextran-DEX, and DEX sulfate-methylcellulose.

In other embodiments, ATPS that exhibit variable phase separation with temperature are utilized. In some embodiments, such systems utilize low molecular weight polymers.

Embodiments of the present disclosure provide ATPS that comprise one or more dehydrated components. In some embodiments, the first polymer comprising the polyanion is dehydrated and is rehydrated by the second solution comprising the polycation.

In some embodiments, all phases of an aqueous two phase system are dehydrated. In such embodiments, the system may be rehydrated using any number of suitable solutions. Examples include, but are not limited to, water or aqueous solution that does not include either of the components of the aqueous two phase system, samples (e.g., blood, urine, serum, semen, saliva or components thereof, etc).

The present disclosure is not limited to a particular method of dehydrating ATPS components. Examples include, but are not limited to, drying or lyophilization. In some embodiments, dehydration is performed in a vacuum at 4° C.-40° C. and rehydration is performed at 4° C.-40° C. for 1 hour to overnight.

In some embodiments, the dehydrated phase(s) is patterned or arrayed on a solid surface. In some embodiments, the support or solid surface is, for example, plastics, metal, glass, paper, fabric, hydrogels, foam, surfaces of sensors, electrodes, cantilevers, microfluidic device surfaces, inside capillaries, on medical devices, etc.

In some embodiments, the surface and reagents are selected to optimize structures for a particular use or shape. For example, in some embodiments, structures are formed with specified shape by defining the shape of the dehydrated polymer solution on the substrate. This may be achieved through surface patterning or by 'drawing' the solution (e.g., via a pipette tip) to fill a desired footprint. In some embodiments, structures are printed by sequential deposition of first and second polymers on solid supports. In some embodiments, structures are formed as a surface-coating on nano- and/or micro-scale beads (e.g., PDMS microspheres).

In some embodiments, structures are formed as self-assembling microspheres wherein uniform droplets of a first polymer solution are introduced in a controlled manner to a solution comprising a second polymer (e.g., using a microfluidic device with separate input channels).

The present invention further provides systems and kits comprising the macromolecular structures described herein. In some embodiments, systems and kits comprise multiple solutions for forming structures (e.g., in solution or dehydrated on a solid support), transport components (e.g., robotics), test compounds, and detection reagents. In some embodiments, kits further comprise additional components useful, necessary, or sufficient for performing and analyzing the results of the methods described herein (e.g., including, but not limited to, buffers, nucleic acids, candidate drug compounds, antibodies, proteins, etc.).

In some embodiments, kits and systems comprise a solid support pre-spotted with a dehydrated first polymer solution comprising a polyanion (e.g., multiwell assay plate(s) such as 96- or 384-well plates) comprising dehydrated nucleic acid DEX droplets that are pre-spotted within each well and a rehydration solution containing a second polymer and a polycation (e.g., 10% PEG (w/w) and selected cationic components such as poly-L-lysine, specific histone subunits, species-matched histones, etc.) or combination of such components). In some embodiments, the polycation is provided as a powder, or lyophilized, to be reconstituted before use by the end user. The end user then reconstitutes the dehydrated first polymer and forms the macromolecular structure.

In some embodiments, kits comprise already formed dehydrated macromolecular structures (e.g., spotted on a solid support). In such embodiments, a rehydration solution is provided as part of the kit or is provided by the end user. The end user then rehydrates the structures prior to use.

The compositions, kits, and systems described herein find use in a variety of research, screening, and clinical applications.

In some embodiments, the uses described herein utilize structures comprising additional components that have been associated with analogous DNA-histone structures, or their producing cells, in vivo. These include, but are not limited to, neutrophil elastase, myeloperoxidase, bactericidal permeability increasing protein, cathepsin G, gelatinase, histones (octamer, as well as individual subunits, and Histone H1), histones (e.g., proteolytically-degraded), histones (post-translationally modified, e.g., citrullinated), histone H2B-Like protein, lactoferrin, lactotransferrin, azurocidin, defensins (e.g., defensin 1, defensin 3), lysozyme C, proteinase-3, pentraxin 3, myeloid cell nuclear differentiation antigen, 5100 calcium-binding protein (e.g., A8, A9, A12), myosin-9, α-Actinin (e.g., 1 and/or 4), plastin-2, cytokeratin-10, catalase, α-Enolase, transketolase, acid (3-glycerophosphatase, acid mucopolysaccharide, al-antitrypsin, α-mannosidase, (3-glucuronidase, N-Acetyl-β-glucosaminidase, sialidase, ubiquitin, (32 microglobulin, collagenase, CRISP-3, hCAP-18, LL-37, histaminase, heparanase, neutrophil gelatinase-associated lipocalin (NGAL), urokinase-type plasminogen activator, transcobalamin-1, acetyltransferase, presenilin-1, stomatin, V-Type H+-ATPase, CD Proteins (10, 11b, 13-16, 18, 45, 66-68), cytochrome b558, fibronectin-R, G-Protein (α Subunit), laminin-R, leukolysin, NB1 Antigen, Rap (1 and 2), SCAMP, SNAP-23, VEGF, FGF, HB-EGF, SNAP-25, thrombospondin-R, TNF-R, uPA-R, CAMP-2, citronectin-R, DAG-deacetylating enzyme, NRAMP-1, alkaline phosphatase, CR-1, Clq-Receptor, decay-accelerating factor (DAF), IL-26, CXCL-12, or CRAMP (see Faurschou M, Borregaard N. Microbes and Infection. 2003 November; 5(14):1317-1327; Urban C F, et al. PLoS Pathogens. 2009 Oct. 30; 5(10):e1000639. Brinkmann V, et al. Science. 2004 Mar. 5; 303(5663):1532-1535).

In some embodiments, the compositions and methods of the present disclosure find use in drug screening and research applications. For example, in some embodiments, structures are contacted with a test compound and the effect of the test compound on the structures is determined (e.g., ability to degrade or inhibit formation of the macromolecular structures).

In some embodiments, structures find use in therapeutic applications such as the delivery of therapeutic compositions (e.g., drugs or other agents such as those described herein). In some embodiments, structures are removed following formation (e.g., if formed in vitro) and implanted within tissues, cell cultures or other biologic systems/environments (e.g., to deliver a therapeutic agent).

In some embodiments, structures find use in diagnostic applications such as, for example, a capture substrate for disease-related antibodies found in a biological sample (e.g., blood or blood product) from a subject. For example, in some embodiments, structures described herein (e.g., DNA-histone structures) serve as anti-nuclear antibody (ANA) binding substrate. In other examples, structures formed from DNA (e.g. circular dsDNA) and a polycation (e.g. polyimmine) that is not histone or other biomolecules can produce structures that are more specific for binding anti-double strand DNA antibodies (anti-dsDNA) from blood (e.g., with less binding of other ANAs). In other examples, RNA-ribonucleoprotein structures are formed and used to specifically detect anti-nuclear riboprotein antibodies (anti-nRNP). In other examples, structures formed from histones (e.g., H2A and H2B complex) and a polyanion that is not DNA can produce structures that are more specifically bound by anti-histone antibodies but not other ANAs. In some embodiments, structures are produced from polycations and polyanions that are much more specific for certain types of ANA compared to use of whole nuclei from cells (e.g., HEp-2 cells).

Experimental

The following examples are provided in order to demonstrate and further illustrate certain preferred embodiments and aspects of the present disclosure and are not to be construed as limiting the scope thereof.

Example 1

Methods

This example describes NET-like DNA-histone structures formed in a microwell plate to enable high-throughput assays including, but not limited to, those delineated in Example 2 and Example 3 below.

Here, a solution containing DNA and DEX was dehydrated on a hydrophobic surface to form a dried polymer spot (FIG. 1A). When a second solution containing histones and PEG was added (FIG. 1B), the DNA-DEX spot rehydrated to reform a DNA-DEX droplet surrounded by the histone-PEG solution. In addition to rehydrating the dried DNA-DEX spot, the PEG solution also supplies histones that are able to complex with the DNA present in the DEX droplet (FIG. 1C).

This technique, and the structures yielded through its use, provide several advantages over existing methods that rely on the use of primary cells. Published protocols for the generation of cell-derived NETs require at least 5 hours to isolate neutrophils and induce NETosis (Brinkmann V, et al., Science. 2004 Mar. 5; 303(5663):1532-1535; Brinkmann V, et al., Journal of Visualized Experiments. 2010 Feb. 24 [cited 2015 Jun. 2]; (36)). Subsequent NET isolation, aggregation, and the dispensation of these aggregate structures into microwells may add an additional day or more to this procedure. Given the short lifespan of neutrophils (<24 h) ex vivo, the time required for these protocols presents a practical challenge for obtaining NETs in a reliable manner for large-scale biological studies. Furthermore, the cost associated with the use of primary cell-derived NETs can be prohibitive in the context of high-throughput assays. The animal cost alone to generate NETs in all wells of a 96-well plate totals >$600 and may increase further (even up to 10× more) depending upon the protocol used and the per-well quantity of NETs required. In addition to the cost and practical limitations of primary cell-derived protocols, the structures they yield are heterogeneous (in shape and density), difficult to handle, and inherently non-uniform in their composition due to the presence or absence of proteins and other particles that may become incorporated or adsorbed to the structure during the NET isolation and handling steps.

Figure 5:
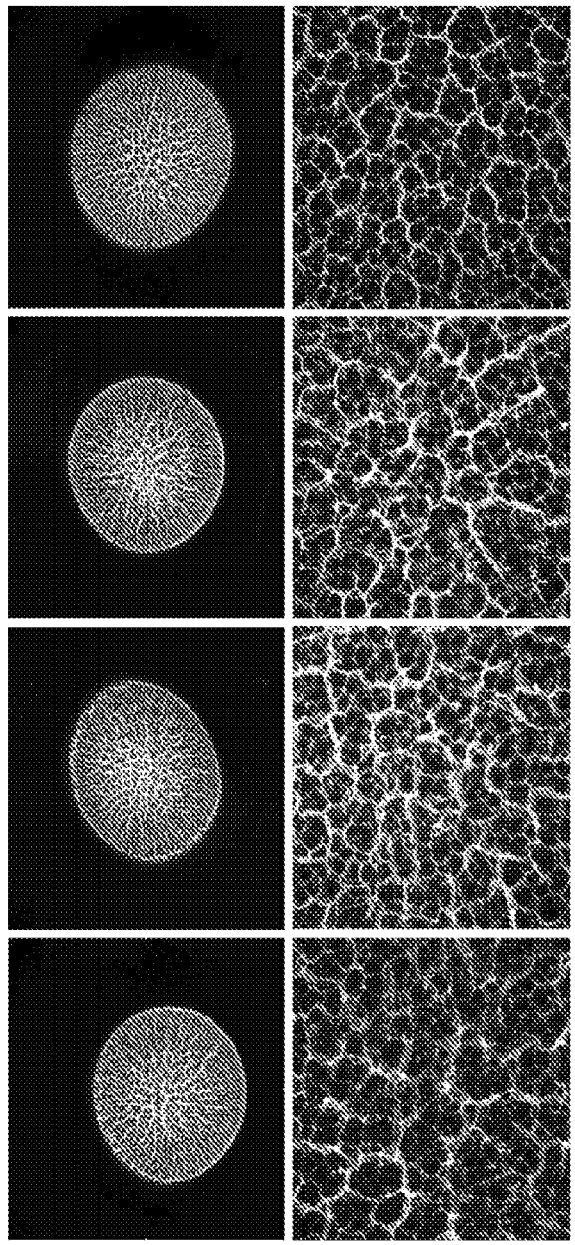
FIG. 5 shows representative images of four replicate DNA-histone structures formed using ATPS platform (formulation: 10% PEG 35 kDa/10% DEX T500). The structures are highly reproducible and minimally heterogeneous at both the macro- (upper panels) and micro-scales (lower panels).
Figure 8:
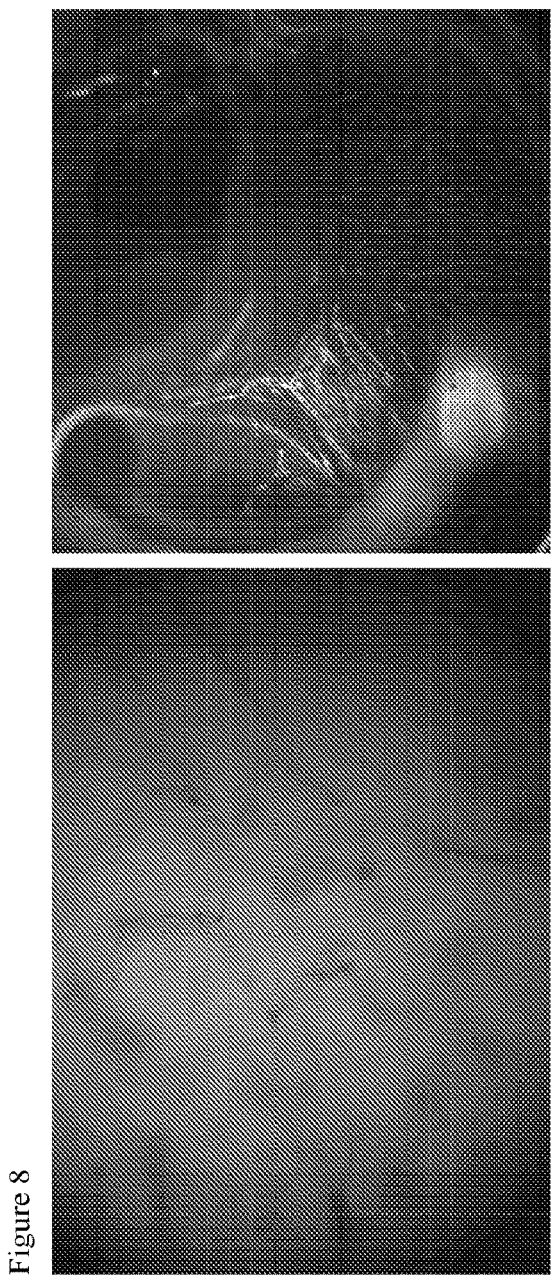
FIG. 8 shows two representative images of the insoluble precipitates with inconsistent overall shapes that form when DNA and histones are combined in 'bulk' (without the use of ATPSs).

In contrast, the method described herein allows users to generate on-demand NET-like DNA-histone structures in 3-4 hours by pipetting a histone-PEG solution into an inexpensive 96-well plate pre-spotted with DNA-DEX and washing out the PEG and DEX solutions prior to use. This approach also permits user-defined incorporation of additional NET-associated proteins (by simply adding the desired proteins to the histone-PEG solution) while also affording precise control over the macro-scale geometry of the structure (FIG. 5). It is important to note that simply mixing bulk solutions of DNA and histones, or rehydrating a dried DNA droplet with a histone solution does not generate well-defined and reproducible structures (FIG. 8).

Modulation of the relative concentration of each component, as well as the properties of the substrate, enable control over the size and density of the resulting DNA-histone structures (e.g., shorter (<3 kbp) DNA forms ostensibly denser meshes), closely mimicking the morphology of endogenous NETs produced by neutrophils. The desired diameter of the final DNA-histone structure (e.g., 0.5 mm, 1 mm, 2 mm, 5 mm) may be obtained by modifying the initial DNA-DEX spot size through adjustment of the spotting solution volume and viscosity. This is done through the use of different DEX molecular weights (MWs) and concentrations (e.g., DEX T40 (40 kDa) or T500 (500 kDa) at 10-40% w/w). The height of the final DNA-histone structure, which may affect its functional properties, is determined by the volume and contact angle of the DNA-DEX droplet upon rehydration by the PEG solution. These may be modified, and normalized, by adjusting the PEG MW (e.g., 10 kDa or 35 kDa) and concentration (e.g., 5-25% w/w) within the rehydrating solution.

Figure 6:
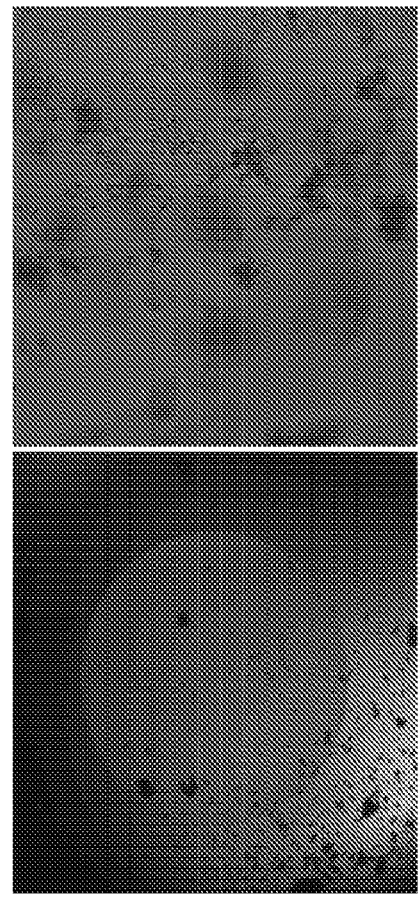
FIG. 6 shows a representative image of a rehydrated DEX droplet within a solution containing >20% PEG. This image is provided to illustrate the phase separation/aggregation of histones observed in certain suboptimal formulations and procedures.
Figure 9:
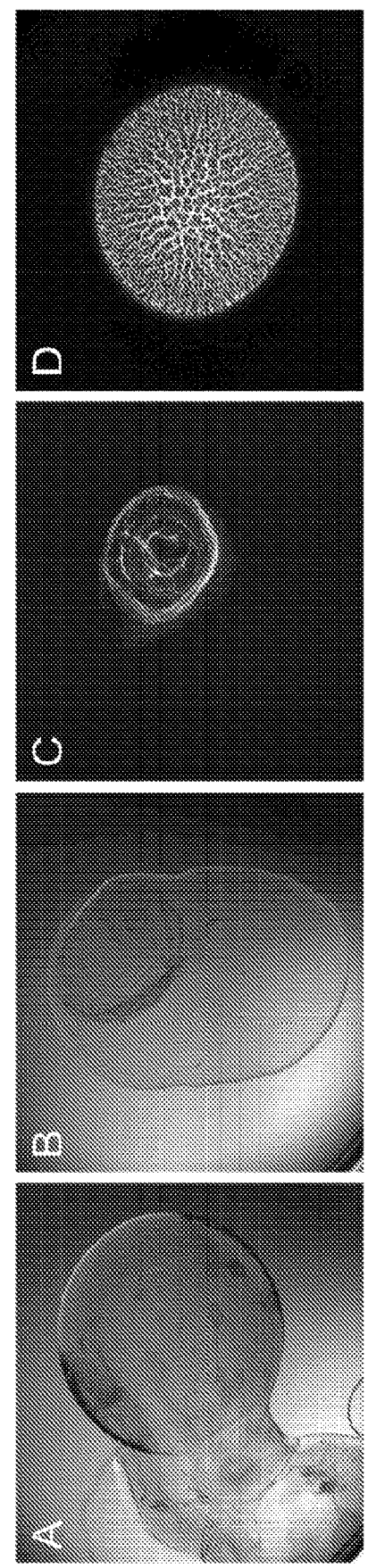
FIG. 9 shows images of DNA and histones combined in the presence of suboptimal ATPS formulations, resulting in structures with reduced circularity (A), ill-defined borders (B), or heterogeneous fiber arrangement (C). Structures formed under optimal ATPS formulations have high overall consistency as characterized by their diameter, circularity, and total fluorescence (D).

It was also found that the ATPS formulation and rehydration procedures are important for achieving reproducible NET-like DNA-histone structures within a microwell format. The table below shows an overview of successful (Y) and unsuccessful (N) ATPS formulations used as well as the broader PEG 35000 and DEX T500 concentrations tested to identify which formulations yielded stable DNA-histone structures (when using other MW PEG and DEX, what concentrations are optimal will shift. In general, larger molecular weight polymers utilize lower concentration whereas smaller molecular weight polymers utilize higher concentrations. In general the concentrations used are above the binodal curve of the phase diagram for ATPS formation). Sub-optimal concentrations of either component, if sufficient to form visible complexes, yielded either phase-separated aggregates (FIG. 6) or structures that were heterogeneous and non-uniform (FIG. 9A-C). The data presented is based upon experiments performed in 96 well plates, and where n>6 for all pairwise conditions.

|  | PEG Percent | | | | | |
| --- | --- | --- | --- | --- | --- | --- |
|  | 5 | 10 | 15 | 20 | 25 | 30 |
| Mammalian DNA (Calf Thymus) | | | | | | |
| DEX Percent 5 | Y | Y | Y | N | N | N |
| 10 | Y | Y | Y | N | N | N |
| 15 | Y | Y | Y | N | N | N |
| 20 | Y | Y | Y | Y | N | N |
| 25 | Y | Y | Y | Y | N | N |
| 30 | Y | Y | Y | Y | N | N |
| Non-Mammalian DNA (λ-Phage) | | | | | | |
| DEX Percent 5 | Y | Y | Y | Y | Y | N |
| 10 | Y | Y | Y | Y | Y | N |
| 15 | Y | Y | Y | Y | Y | N |
| 20 | Y | Y | Y | Y | N | N |
| 25 | Y | Y | Y | N | N | N |
| 30 | N | Y | Y | N | N | N |

Measures of droplet uniformity include, but are not limited to, circularity (as determined using the isoperimetric quotient) and diameter of DNA-DEX spots. These may be measured before and after spot rehydration.

Figure 2:
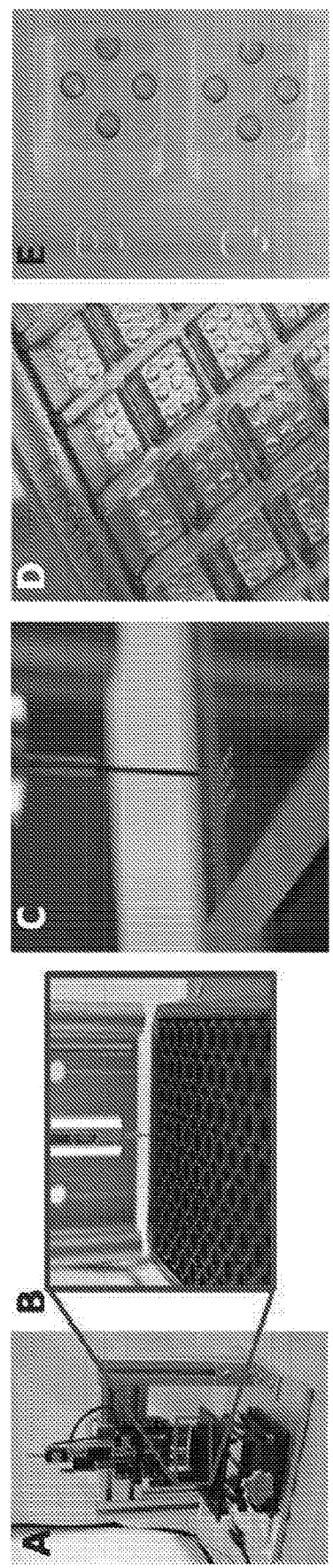
FIG. 2 shows high throughput and consistent spotting of viscous solutions. (A) Custom automated platform for spotting viscous solutions. (B) Close up image of the dispensing tip approaching a 96 well plate. (C) Close up of nine arrayed 250 nL droplets on a polycarbonate sheet (D) Custom plates (manufactured by PHASIQ) with nine 1.7 mm dimples on the floor of a 96 well format microwell. (E) Two microwells shown with blue DEX droplets spotted and dried within four of the nine dimples in each microwell. The DEX spots are well defined by the dimples.

The scaled production of reproducible and uniform NET-like DNA-histone structures may be achieved through the use of custom systems capable of consistently spotting small volumes of highly viscous DNA-DEX solutions. FIG. 2 shows one such spotting machine and custom plates that confine spotted droplets for this purpose.

A sample protocol utilized for the formation of the described DNA-histone structures is provided below.

DNA-DEX Droplet Dehydration 2 mg/ml calf thymus DNA (13 kbp) and 20% w/w DEX T500 were prepared in PBS. DNA and DEX solutions were then mixed at a volume ratio of 1:1. 5 µL of the resulting mixture was then dispensed into each well of a 96-well plate (n=36 wells/plate). The plates were left under vacuum overnight for dehydration.

DNA Histone Structure Rehydration and Nucleic Acid Staining:

2 mg/ml calf thymus histones (Type II-A) and 20% w/w PEG (MW 35 kDa) were prepared in PBS. The histone and PEG solutions were then mixed at a volume ratio of 1:1, and 200 µL of the resulting mixture was added into each well of the previously-prepared 96-well plate (pre-seeded with droplets of dehydrated DNA-DEX). Following incubation (approximately 3 hrs) at room temperature, 150 µL of supernatant was removed from each well, and each well was washed (4-5 times) with 150 µL of PBS to remove the PEG and DEX polymers. After completing these serial wash steps, 2-3 µL of 7.2 mM DAPI or 500 µL Sytox Green was added to each well and incubated overnight at 4° C. 150 µL of solution was removed the following day, and the stained structures were washed (4-5 times) with 150 µL of PBS. Brightfield and fluorescence images of the DNA-histone structures were gathered immediately following washing steps. This protocol has also been followed to form DNA-histone structures with λ-Phage DNA.

Example 2

Drug Screening Methods

This example presents an embodiment wherein DNA-histone structures are utilized to screen pharmaceutical or naturally-occurring compounds capable of degrading or suppressing the degradation of NETs in vivo.

The degradation of NETs by bovine pancreas deoxyribonuclease I (DNase I) was initially performed to confirm the presence and primacy of DNA in the overall NET architecture (Brinkmann V, et al., Science. 2004 Mar. 5; 303(5663): 1532-1535). Subsequent work has demonstrated the physiological relevance of nuclease-mediated degradation, as nucleases present in serum have been found to degrade NETs (Köckritz-Blickwede M von, et al., Blood. 2009 Dec. 10; 114(25):5245-5246. PMID: 20007813), and pathogens such as Group A *Streptococcus* have evolved to secrete nucleases that may free them from entrapment by these structures (Buchanan J T, et al., Current Biology. 2006 February; 16(4):396-400; Beiter K, et al., Current Biology. 2006 February; 16(4):401-407). Nuclease-mediated degradation, consequently, has served as a template for developing therapies for several NET-associated pathologies including myocardial ischemia/reperfusion injury (Ge L, et al., American Journal of Physiology—Heart and Circulatory Physiology. 2015 Mar. 1; 308(5):H500-H509). Genentech has developed a recombinant DNase, Pulmozyme, intended for the treatment of cystic fibrosis (Shak S, et al., PNAS. 1990 Dec. 1; 87(23):9188-9192), and applications for this and other related compounds for the treatment of systemic lupus erythematosus (Macanovic M, et al., Clinical & Experimental Immunology. 1996 Nov. 1; 106(2):243-252) are currently under development.

By extension, compounds capable of modifying nuclease-mediated degradation may be pathogenic or therapeutic (Lande R, et al., Science Translational Medicine. 2011 Mar. 9; 3(73):73ra19-73ra19; Ge L, et al., American Journal of Physiology—Heart and Circulatory Physiology. 2015 Mar. 1; 308(5):H500-H509; Macanovic M, et al., Clinical & Experimental Immunology. 1996 Nov. 1; 106(2):243-252). For example, LL-37, which is the neutrophil-derived cleavage product of the human cathelicidin hCAP-18, has been shown to directly bind to NETs and protect them from nuclease-mediated degradation, thus contributing to host immune defense (Neumann A, et al., Journal of Innate Immunity. 2014; 6(6):860-868). In order to validate that our DNA-histone structures recapitulate properties of NETs in terms of their susceptibility to nuclease-mediated degradation and interaction with known modifiers of nuclease-mediated degradation, we performed a series of experiments wherein DNAse I-mediated degradation was characterized in the presence and absence of LL-37.

Figure 3:
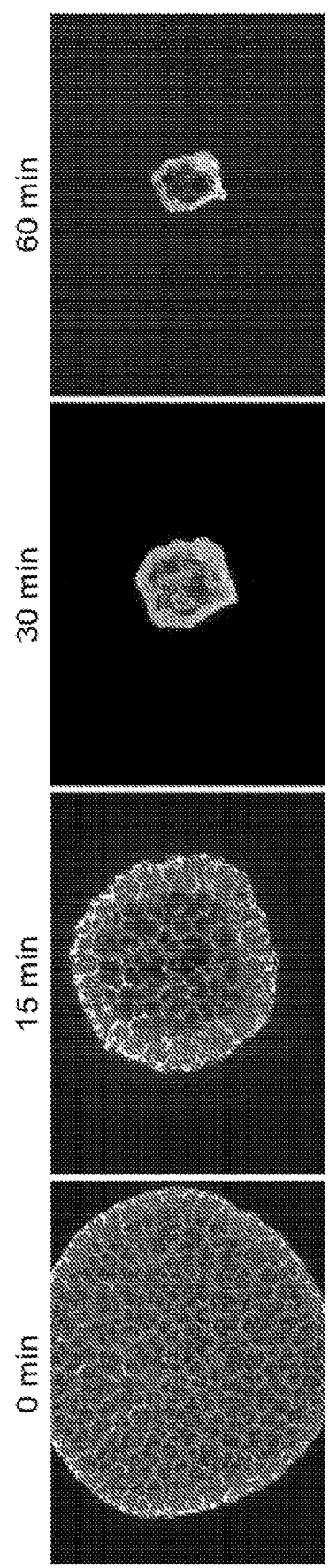
FIG. 3 shows DNase I-mediated degradation of DNA-histone structures. Structures were stained with the nucleic acid-intercalating fluorophore Sytox Green and exposed to DNase I (1 mg/ml) for the indicated lengths of time. All images were contrast enhanced in ImageJ to optimally display morphological changes.
Figure 4:
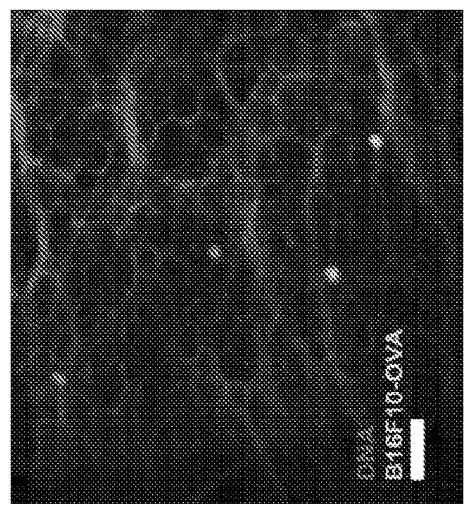
FIG. 4 shows an exemplary platform for exploring cellular interactions with DNA-histone structures.

Time-lapse microscopy and microplate photometry were utilized to measure the overall rate of degradation, and DNA-histone structures were treated with multiple concentrations of DNase I to verify the dose-dependency of this rate (FIG. 3).

Figure 7:
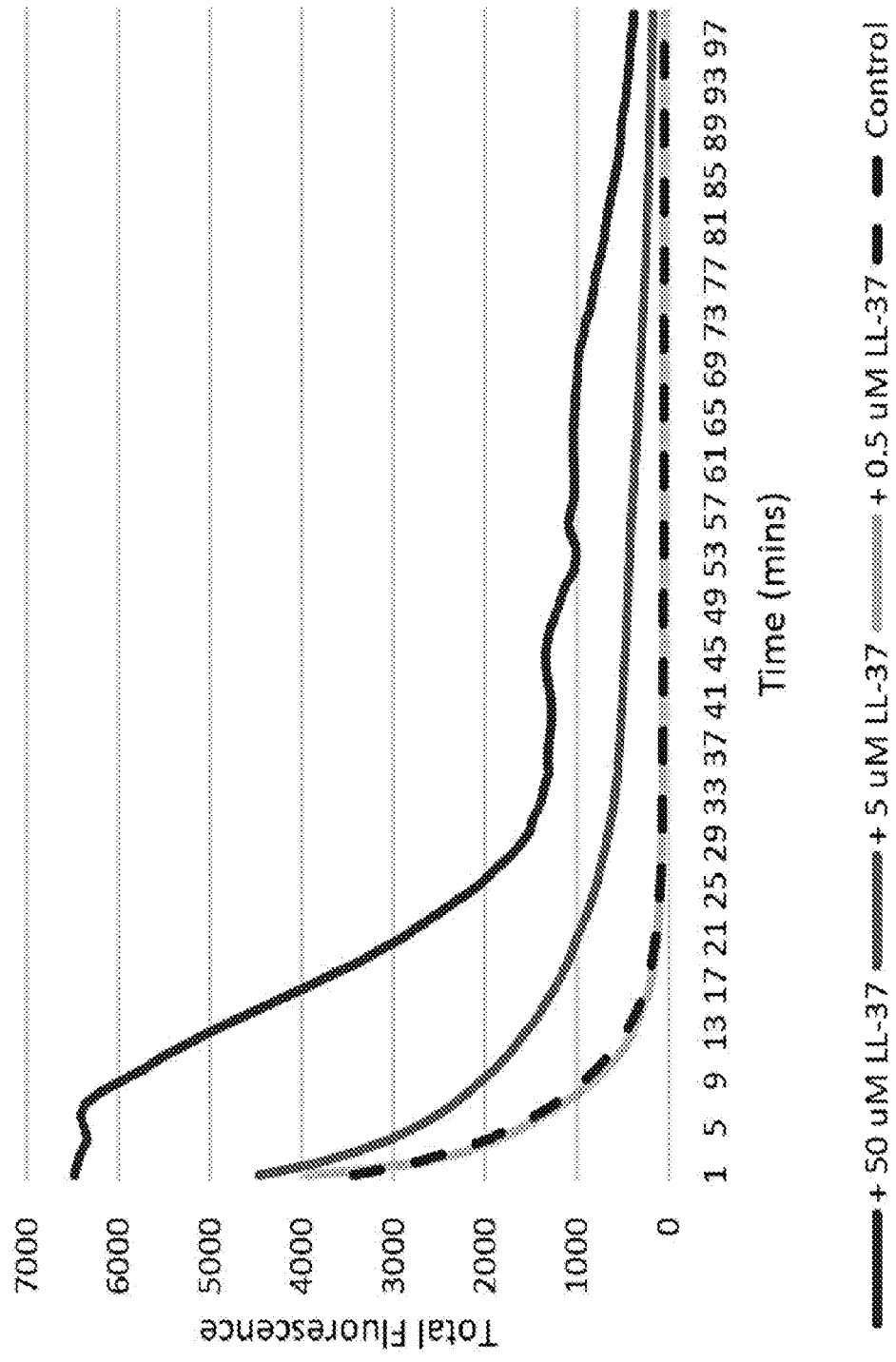
FIG. 7 shows the results of a degradation modifier assay. Here, the indicated concentrations of the known degradation inhibitor LL-37 were added to the structures prior to DNase I exposure. Total Sytox Green fluorescence is displayed to approximate the degree of degradation occurring for each condition (n=3). Preincubation causes LL-37 to bind and inhibit the rate of DNase I mediated degradation of the DNA-histone structures.

These experiments showed a dose-dependent decrease in the overall rate of DNase I-mediated degradation (relative to structures lacking LL-37 that had also been treated with DNase I) and further validated the functional homology between our DNA-histone structures and physiologically-derived NETs (FIG. 7).

These results also provide additional support for the utility of this platform in investigating the relationship of other NET-associated peptides and proteins with DNase-mediated degradation in vitro.

A sample protocol utilized for the formation of the described DNA-histone structures is provided below.

DNase I Preparation and Degradation (without LL-37)

1 mg/ml DNase I (MW 31 kDa) was prepared in 10 mM Tris-HCl, 10 mM $CaCl_2$, pH 7.5 (Tris buffer). Each well containing DNA-histone structures (as previously described) was washed 3 times with 150 μl of Tris buffer, and all solutions within each well were removed. 200 μL of the DNase I solution was then added to each well, and time-lapse fluorescent images of each well were acquired.

Rehydration and LL-37 Incorporation 1 mg/ml LL-37 (MW 4.49 kDa) and 2 mg/ml histones (both in PBS) were added to a solution of 20% w/w PEG/PBS such that the final concentration of histones was approximately 1 mg/ml, and the final concentration of LL-37 in each solution was approximately 0.5 μM, 5 μM, or 50 μM. The effect of LL-37 addition was performed under three conditions: (1) addition of LL-37 before/during DNA-histone structure formation, (2) addition of LL-37 following structure formation (without subsequent washing), and (3) addition of LL-37 following structure formation (with a subsequent wash step).

DNase I Degradation and Image Acquisition

After complete removal of the solutions in each well, 150 μL of DNase I solution was added to each well. Time-lapse images or measurements of total fluorescence were acquired at a rate of one measurement per minute.

Example 3

Screening Methods

Figure 23:
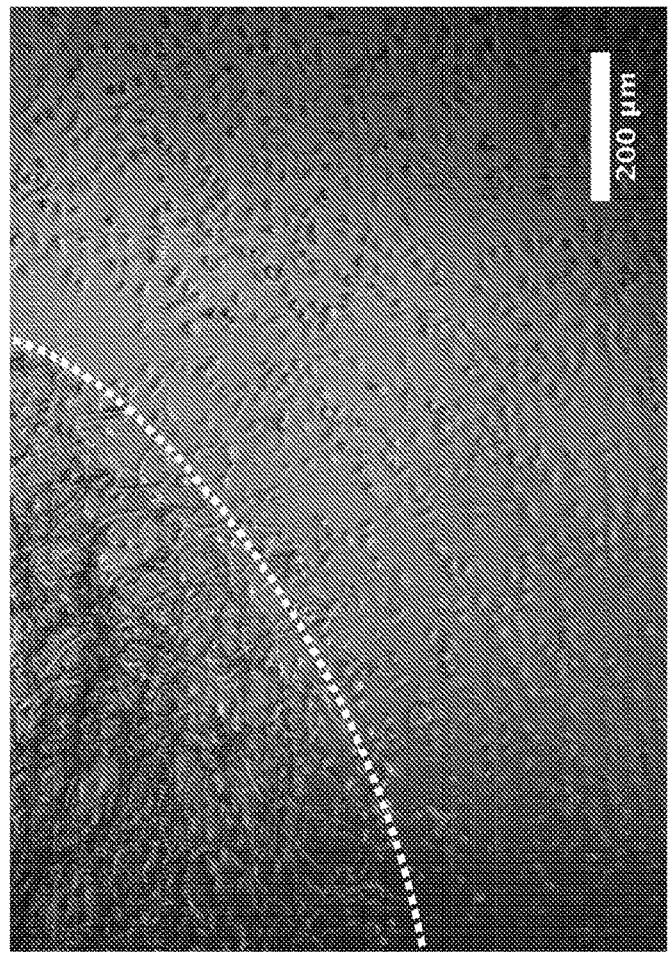
FIG. 23 shows a brightfield image of bone marrow-derived dendritic cell (BMDC) culture with a synthetic NET, the border of which is delineated by the white dotted arc.
Figure 24:
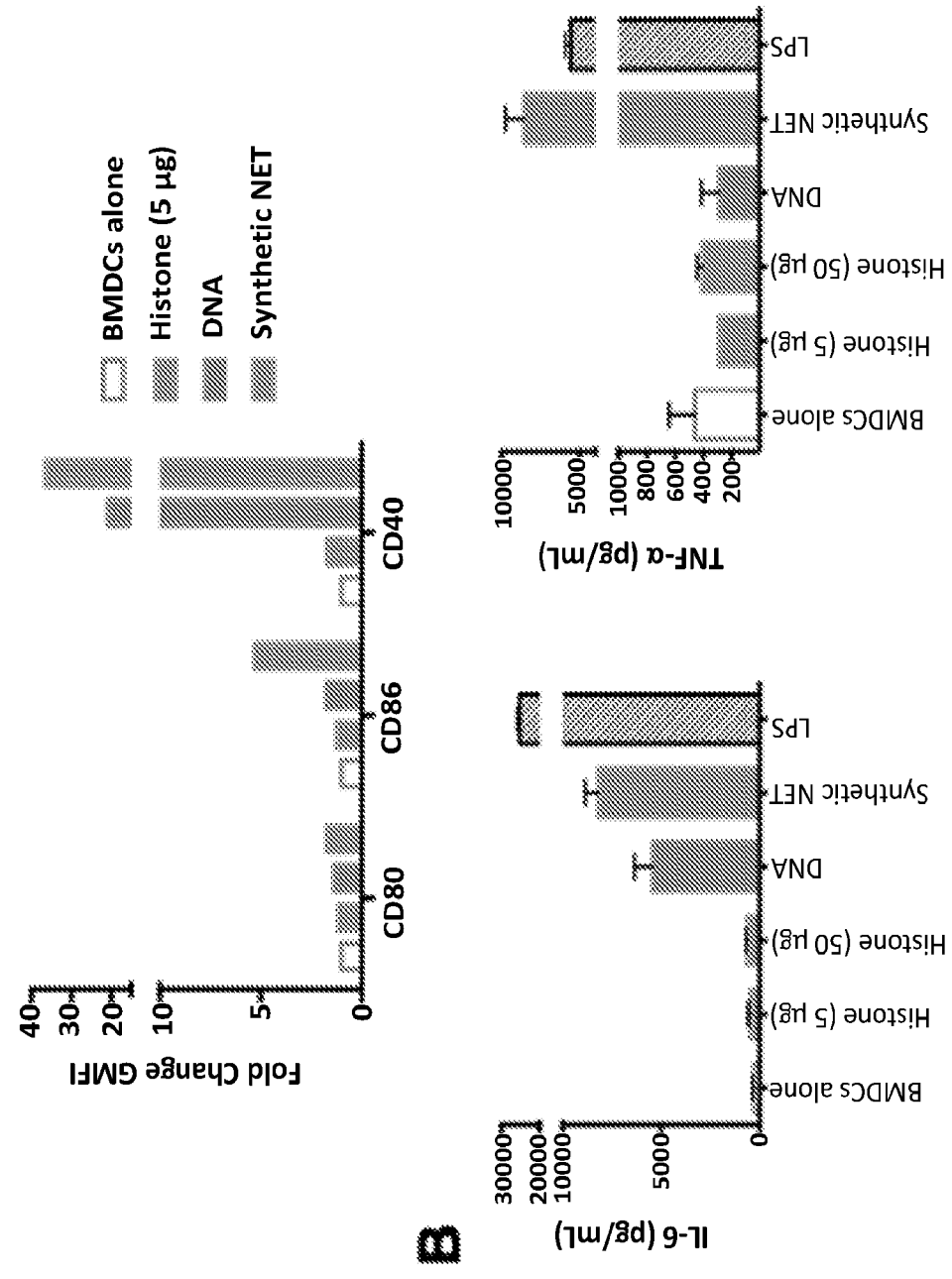
FIG. 24 shows the results of an overnight culture of murine bone marrow-derived dendritic cells (BMDCs) with synthetic NETs, individual component controls, or the positive control 1 µg/mL lipopolysaccharide (LPS). (A) Flow cytometry results for activation markers CD80, CD86, and CD40 on the cultured BMDCs. (B) ELISA results for interleukin-6 (IL-6) and tumor necrosis factor-$\alpha$ (TNF-$\alpha$) and in the supernatants of the culture.
Figure 25:
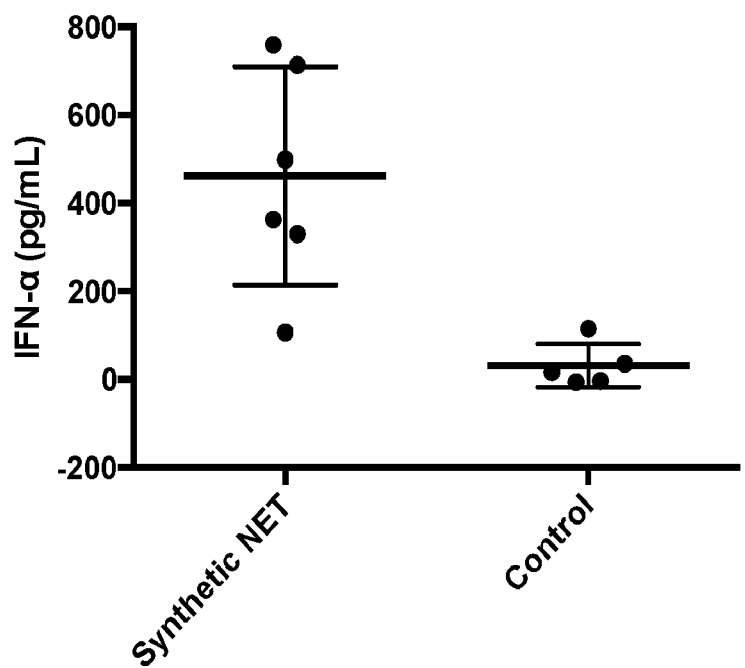
FIG. 25 shows the results of an overnight culture of murine plasmacytoid dendritic cells (pDCs) with synthetic NETs. Interferon-$\alpha$ (IFN-$\alpha$) concentrations in the supernatant were assayed by ELISA.

For example, residual NET structures are thought to induce maturation in dendritic cells (Papadaki G, et al., Eur J Immunol. 2016 Sep. 2) and, in particular, induce potent type I interferon production in plasmacytoid dendritic cells (pDCs) (Lande R, et al., Science Translational Medicine. 2011 Mar. 9; 3(73):73ra19-73ra19). The ability of DNA-histone structures to activate both generic DCs and pDCs was assayed using the well-plate platform presented in Example 1. To this end, dendritic cells were cultured out of the bone marrow of mice (bone marrow-derived dendritic cells, BMDCs), and pDCs were isolated from murine splenocytes. Each cell type was then incubated with DNA-histone structures (FIG. 23) overnight. To assess BMDC maturation and activation, cell surface maturation markers CD80, CD86, and CD40 were assessed by flow cytometry (FIG. 24A), and pro-inflammatory cytokine release (IL-6, TNF-α) into the supernatant was measured by ELISA (FIG. 24B). For pDCs, the release of type I interferon (here, IFN-α) into the supernatant was also measured by ELISA (FIG. 25).

It is hypothesized that the activation of these cellular populations by NETs is mediated by Toll-like receptor 9 (TLR9) engagement (Papadaki G, et al., Eur J Immunol. 2016 Sep. 2; Lande R, et al., Science Translational Medicine. 2011 Mar. 9; 3(73):73ra19-73ra19). Inhibitors of TLR9 such as oligonucleotide ODN TTAGGG are used as both TLR-dependence probes as well as test compounds or therapeutics for diseases in which the immune response is over-reactive (e.g., systemic lupus erythematosus) (Lande R, et al., Science Translational Medicine. 2011 Mar. 9; 3(73): 73ra19-73ra19; Klinman D M, et al., Annals of the New York Academy of Sciences. 2005 Nov. 1; 1058(1):87-95). In some embodiments, the present disclosure therefore provides a high-throughput system by which such modifiers of the interactions between NETs and cells/tissues are screened for their efficacy as therapeutic interventions.

Example 4

Figure 10:
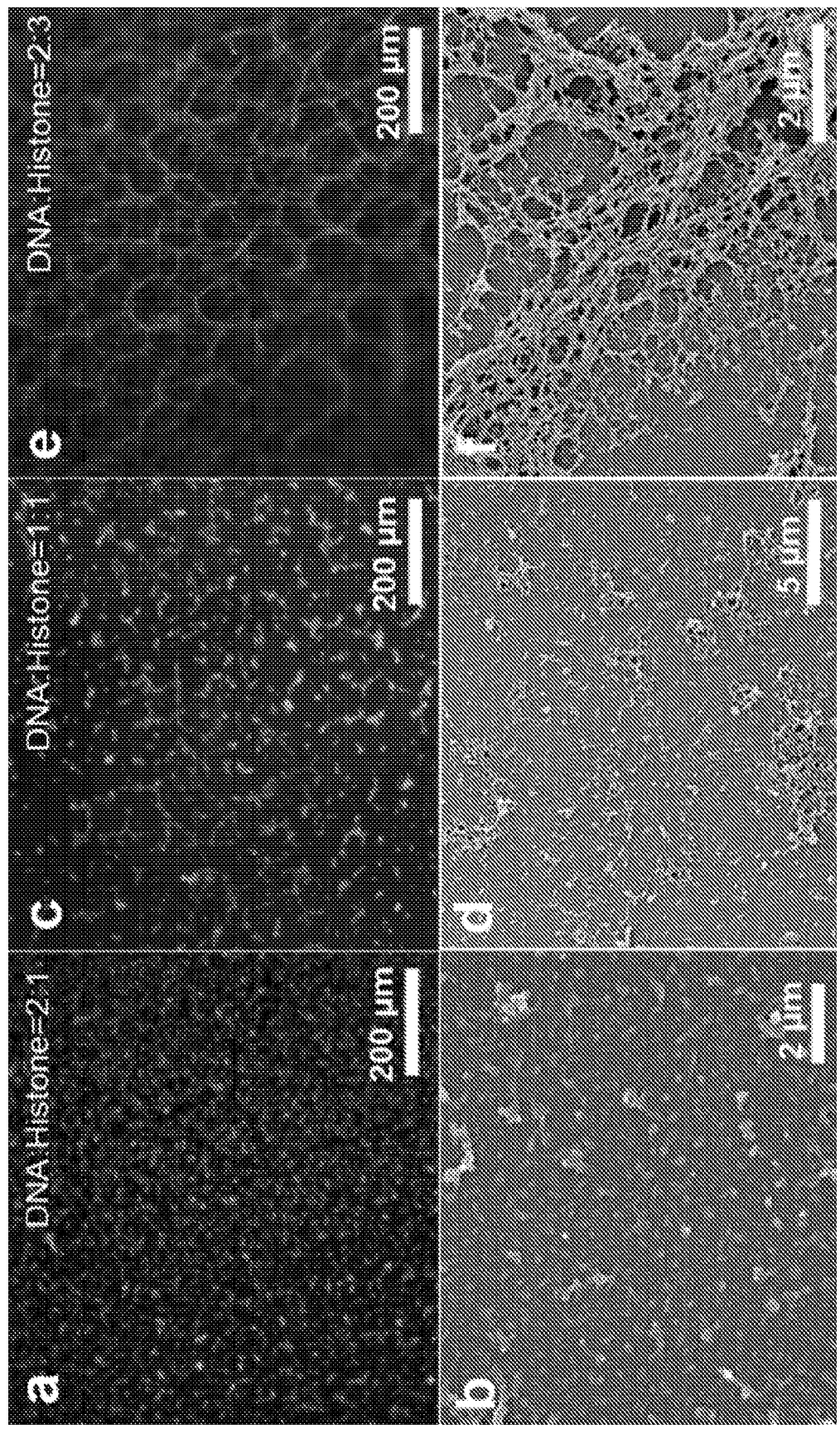
FIG. 10 shows optical and scanning electron microscopy images of DNA/histone nanofiber mesh suspensions formed with different histone concentrations after static standing for 2 hrs. The weight ratio of DNA to histone in the mixtures are (a) and (b) 2:1; (c) and (d) 1:1; (e) and (02:3.

Preparation and Characterization of Synthetic Neutrophil Extracellular Trap (NET) Suspensions Formation of Synthetic NET Structures in Suspension DNA-histone nanofiber meshes were prepared by mixing lambda phage DNA solution (1 mg/ml) with an equal volume of calf thymus histone solution (The buffer solution is Hank's Buffered Salt Solution (HBSS)). The concentration of histone varies from 0.02 to 1.5 mg/ml. After static standing for 2 hrs at room temperature, the synthetic NET suspensions were stained with Sytox green (1:1000 dilution). The individual synthetic NET structures formed are smaller with lower histone concentrations and larger continuous mesh structures form when using higher histone concentrations (FIG. 10).

Formation of Smaller Synthetic NET Structures in Suspension

Periodic pipetting (~every 3 minutes) of the DNA and histone solutions after they are initially mixed in the Eppendorf tube avoids the formation of large mesh structures that can be observed in the static aging approach, particularly at higher histone concentrations. Alternatively, smaller synthetic NET structures can also be obtained by ultra-sonication (5-20 min) of the larger mesh structures. These methods give small synthetic NET structures with reasonably regular shapes. Furthermore, these synthetic NET suspensions can be readily coated onto defined shape particles to give defined shape and size synthetic NET coated particles and cells.

Synthetic NETs can Coat Bacteria. Measurement of Zeta Potentials of the Synthetic NET Structures and Bacteria Coated with Synthetic NETs Fifty μg of synthetic NET structures were dispersed into 1 mL HBSS. The suspension was injected into a folded capillary cell for measurement of zeta potentials with a Zetasizer. One million pathogenic E. coli UT189 cells (100 μL, OD600:0.01) was mixed with the above suspension. After 30 mins, the mixture was centrifuged at 8000 rpm for 2 mins until a pellet of cells was observed at the bottom of the tube. The supernatant was remove and fresh HBSS solution added to a total volume of 1 ml. This wash procedure was repeated 3 times before measuring the zeta potentials of the synthetic NET-coated E. coli with the Zetasizer. The zeta potential of just the the synthetic NETs alone as well as the bacteria coated with synthetic NETs becomes more positive as the ratio of histones is increased.

Figure 11:
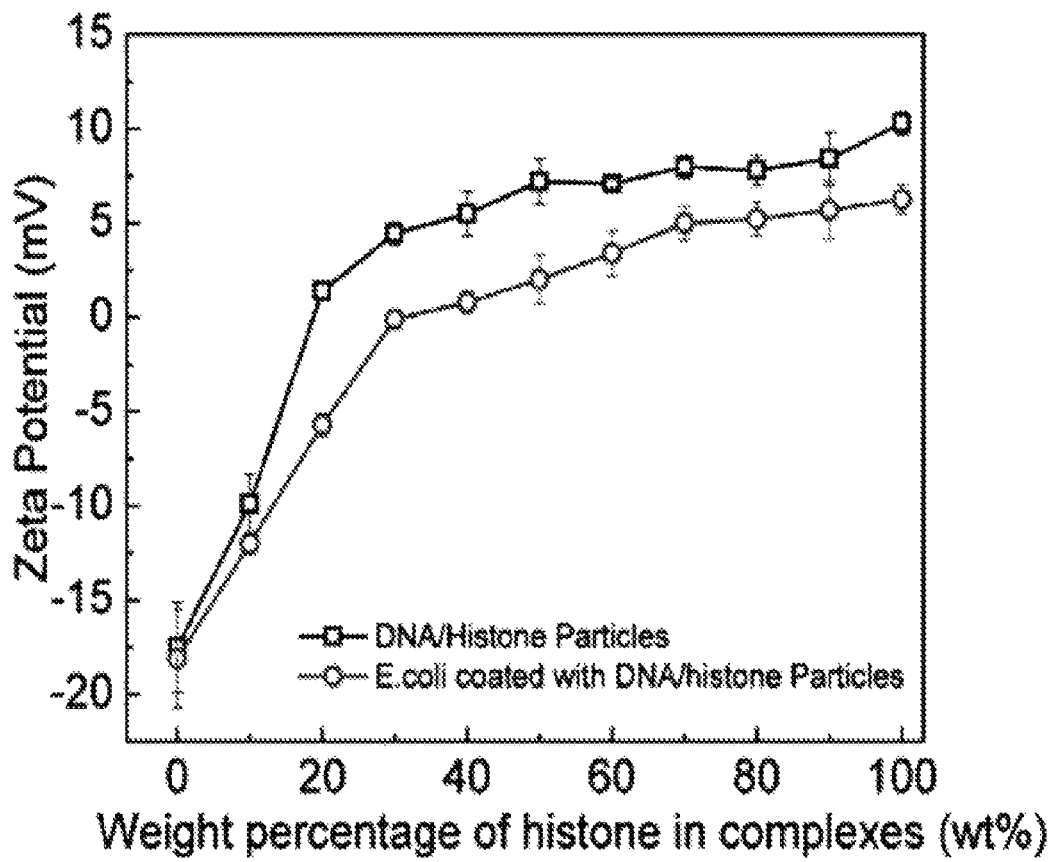
FIG. 11 shows the zeta potential of synthetic NETs and synthetic NET-coated bacteria (E. coli) formed with different DNA/histone ratios.

This procedure also produces bacteria coated NETs with shapes defined in the shape of the bacteria. Similarly, particles other than bacteria can be coated with synthetic NET suspensions to produce defined shape and size synthetic NET particles (FIG. 11).

Preparation of Synthetic Neutrophil Extracellular Trap (NET) Suspensions from DNA/DEX Particles.

Figure 12:
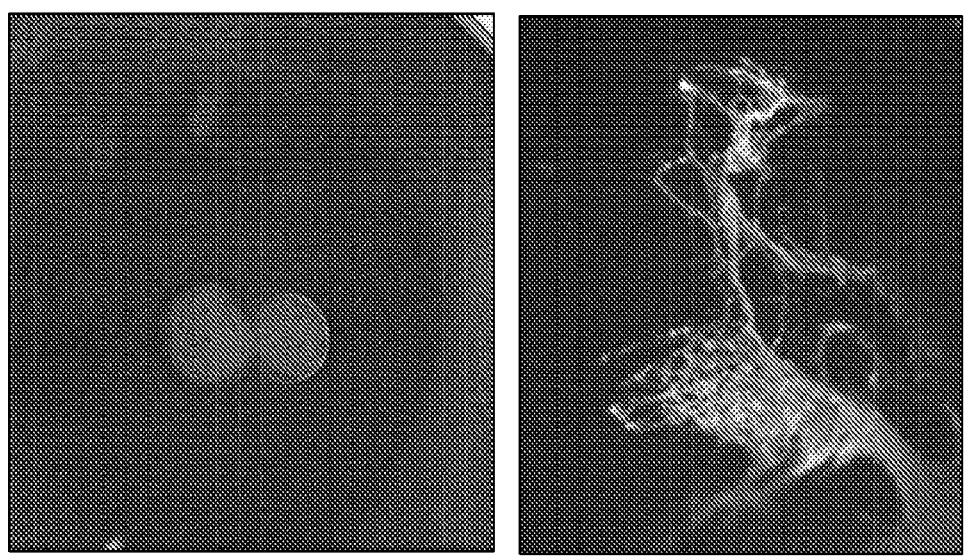
FIG. 12 shows fluorescence images depicting (left) DNA/DEX particles prior to rehydration, and (right) following rehydration with a histone solution.

DNA (0.5-2 mg/mL in DI water) and dextran (5-20 wt %) are dispensed as droplets into a bulk solution (continuous phase) of concentrated polyethylene glycol (low molecular weight PEG, 60-100 wt %). This results in the dehydration of DNA/dextran droplets to form soft DNA/DEX particles. When these particles are transferred into a solution comprised of histones (0.5-2 mg/mL in aqueous buffer) and a lower concentration of PEG (30-80 wt %), the DNA/dextran particles rehydrate and gradually form a mesh comprised of histones and DNA. The mesh starts to form at the particle surface then ultimately extends throughout the interior volume of the droplet that forms from rehydration of the DNA/DEX particle (FIG. 12).

Figure 13:
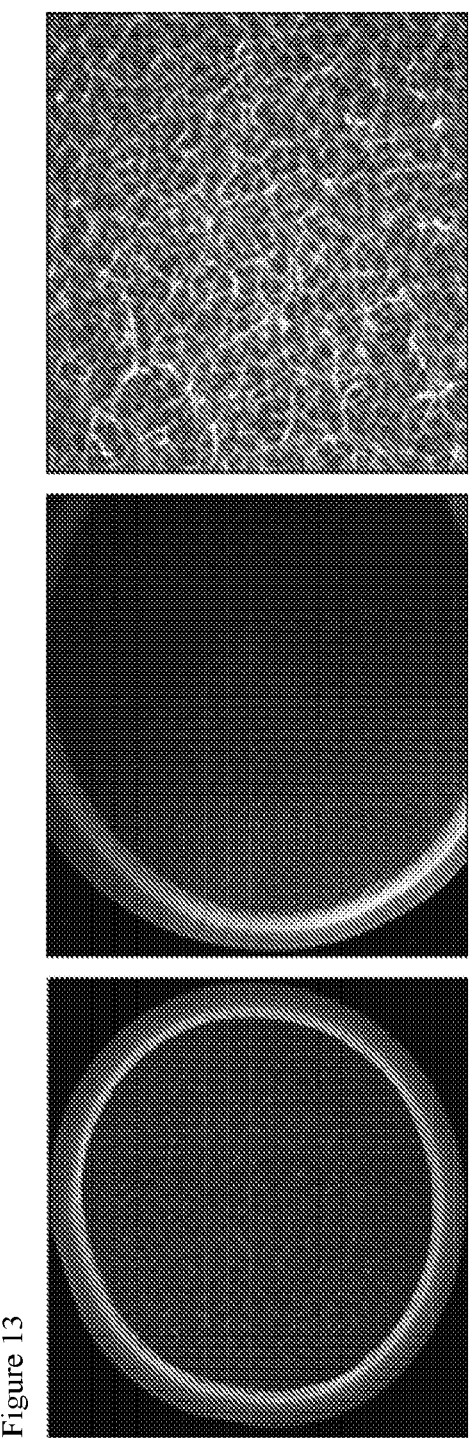
FIG. 13 shows fluorescence images depicting (left and center) the gross morphology, at low magnification, of Sytox-stained DNA:Histone structures, and (right) the fibrous nature of the resulting structure at higher magnification.
Figure 22:
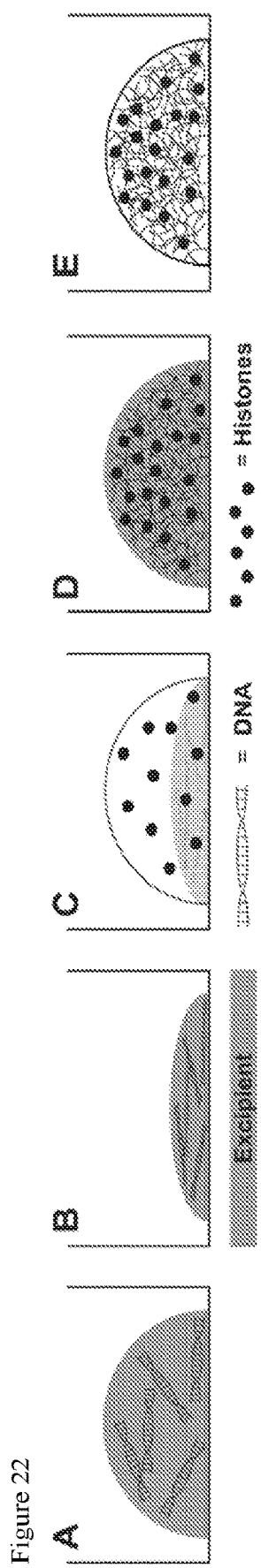
FIG. 22 shows the generation of NET-like DNA-histone structures in the absence of ATPS by utilizing an excipient in dehydration. (A) DNA-excipient droplets are pre-spotted in a microwell plate. (B) DNA-excipient spots are dehydrated. (C) A droplet of equal volume containing histones is added on top of the DNA-excipient spot. (D) DNA-histone structures form via slow controlled diffusive mixing. (E) Structures are washed, removing the excipient.

Preparation of Surface-Attached Synthetic Neutrophil Extracellular Traps (NETs) with Well-Defined Overall Shapes from Dehydrated Spots of DNA and Small Molecule Excipient DNA (<2 mg/mL, for example 270 μg/mL, in DI water) and trehalose (400-800 mM in DI water) were combined and dispensed as droplets ranging from 0.1-40 μL onto a desired substrate. The droplets were then placed under vacuum (or left at room temperature) to dehydrate/vitrify. When droplets have fully dried, they were rehydrated by addition of either a droplet of equal volume of histone octamer (<2 mg/mL, for example 250 ug/mL, in aqueous buffer such as tris and pbs), or by complete submersion of the dehydrated DNA spot into a large volume of the histone solution. Following completion of rehydration and formation of the DNA/histone mesh structures, the structures were washed using fresh buffer or DI water. Structures are shown in FIG. 13. Schematic of the method is shown in FIG. 22.

Preparation of Synthetic NETs on Porous Substrates

DNA-histone structures may be formed on porous membranes for purposes including, but not limited to, the fabrication of wound dressings.

The methods are similar to those described previously for the formation of DNA-histone structures within multiwall plates; but differs in that the porous material (e.g. polycarbonate or polyvinyl filter membranes) must be in direct contact with a hydrophobic material (e.g. PDMS) underneath in order to prevent leaking/transit of the DNA-trehalose solution that is initially deposited on the surface of the porous material. Following deposition of the DNA-trehalose solution; the droplet(s) must then be dehydrated (to allow for complete drying), and rehydrated using an aqueous histone solution. It is important, during rehydration, to also ensure the porous material is placed in direct contact with a hydrophobic material to prevent/minimize loss of the histone solution to trans-membrane leaking.

Figure 14:
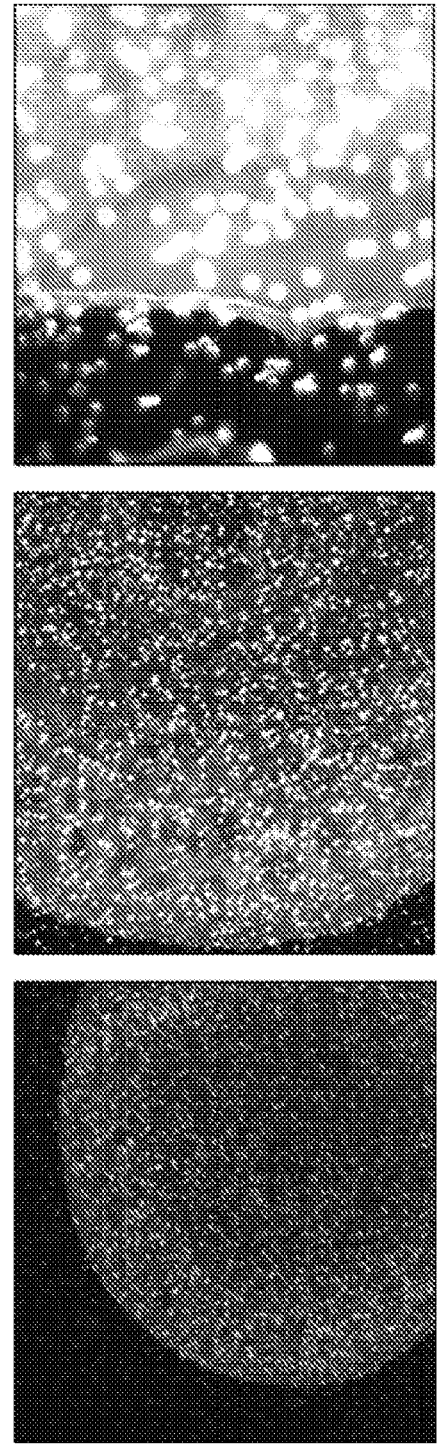
FIG. 14 shows optical micrographs of DNA-histones structures formed using the methods of embodiments of the present disclosure on porous polycarbonate membrane filters (at increasing magnification, from left to right).

Following formation of the DNA-histone structures; additional components (e.g. silver nanoparticles) may be incorporated within the structure by depositing small volumes of these component suspension solutions on top of the DNA-histone structures. These structures must then be allowed to incubate with the component suspension solution, and following any desired/required washes; may then be utilized for subsequent experiments and work. Structures are shown in FIG. 14.

Preparation of Synthetic Neutrophil Extracellular Trap (NET) that Incorporate Additional Components Such as Human Neutrophil Elastase, Cathepsin G, and LL-37.

The procedure outlined below was utilized for the incorporation of Neutrophil Elastase (HNE), LL-37, PAD-4, Cathepsin-G, and CL-amidine. The source material (if lyophilized, or provided in powdered form) is first dissolved in an aqueous buffer solution (the specific composition of this solution is dependent upon the chemical structure of the component being solubilized), and is then either used immediately, or stored at 4° C. until needed. It is important that the final solution have a pH that is below (approximately) ~10. Solutions with pH values exceeding this value may be utilized, but produce significant changes in the morphology of the structure owing to histone charge inversion.

If the source material is not lyophilized, or in powdered form, it is used directly. The resulting solution is either combined with the rehydrating histone solution to allow these components to compete with histones during formation of the fibrous structure; or added following rehydration of the structure by the histone solution. If added through combination with the rehydrating histone solution; it is important that the final concentration of histones remain >1 mg/mL. Concentrations of histone below this produce DNA-histone structures, but they appear less uniform morphologically. Conversely, if added following rehydration, it is best to gently extract all of the histone buffer solution from each well, and to 'wash' the structure gently using buffer or DI water to remove as much unbound histone as possible. Following these washes, all liquid should be extracted from each well, at which point the solution containing any non-histone component(s) may then be added.

Figure 15:
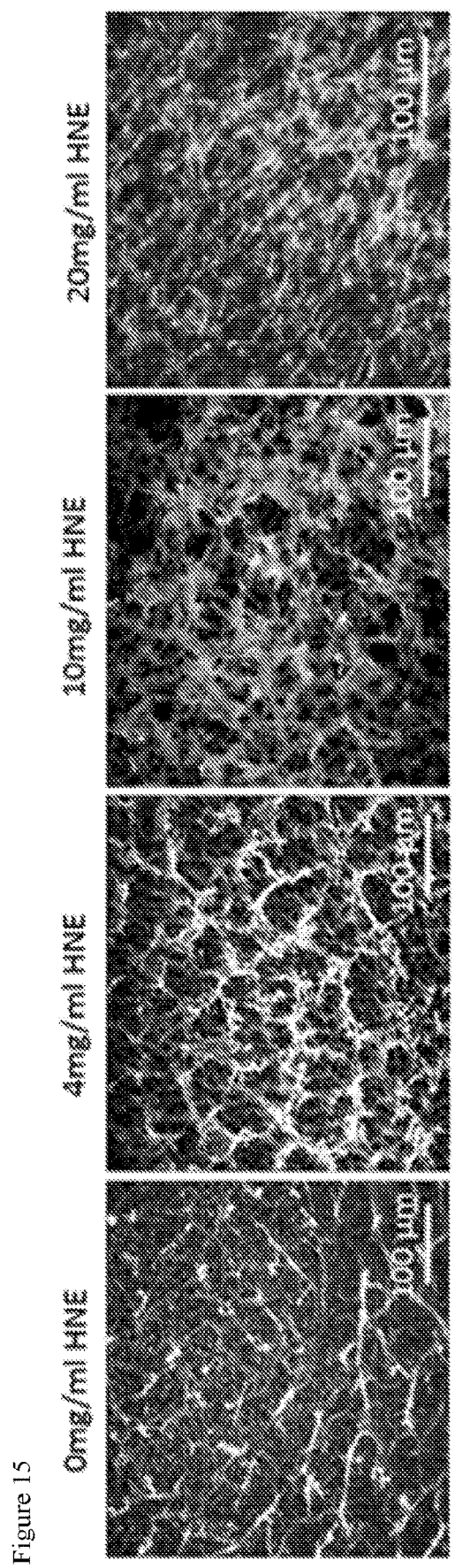
FIG. 15 shows optical Microscope images of the morphology of the DNA/histone complex after incorporation of human neutrophil elastase at different concentrations for 3 hrs.

Subsequent washing steps can be used to minimize the presence of unbound material; but are dependent on the specific protocol or experimental procedure being applied. This technique has enabled, to date, (a) the incorporation of enzymes, and monitoring of their activity following incorporation within the DNA-histone structure (FIG. 15), (b) the incorporation of biomolecules (e.g. LL-37) that are able to interfere with the enzymatic degradation of the DNA component of the DNA-histone structure, and (c) the incorporation of selective inhibitors/antagonists (e.g. CL-amidine) capable of modulating the activity of soluble (free) enzymes present within the medium surrounding the DNA-histone structures.

Example 5

Uses of Synthetic NETs

Anti-Bacterial Function
Synthetic NETs Inhibit Bacteria Growth as Measured by Optical Density Synthetic NETs were formed by mixing 30 μL DNA solution (1 mg/ml) with different concentration of histone solutions (0-1 mg/ml, 304) in 96 well plates. An additional 40 μL of HBSS was also added to each well. After letting the mixture sit for 2 hrs, one million pathogenic *E. coli* UT189 cells (*E. coli* were dispersed in 100 μL Tryptic Soy Broth containing 1% Glucose (TSBG) media with a corresponding OD value of 0.01 at 600 nm) were mixed with the prepared synthetic NET suspension. The growth curves of the *E. coli* were measured using the optical density at 600 nm over 6-16 hrs. During the measurements, the temperature was maintained at 37° C. The 96 well plate was shaken for 15 seconds before taking each measurement. The time interval between readouts was 10 mins.

Figure 16:
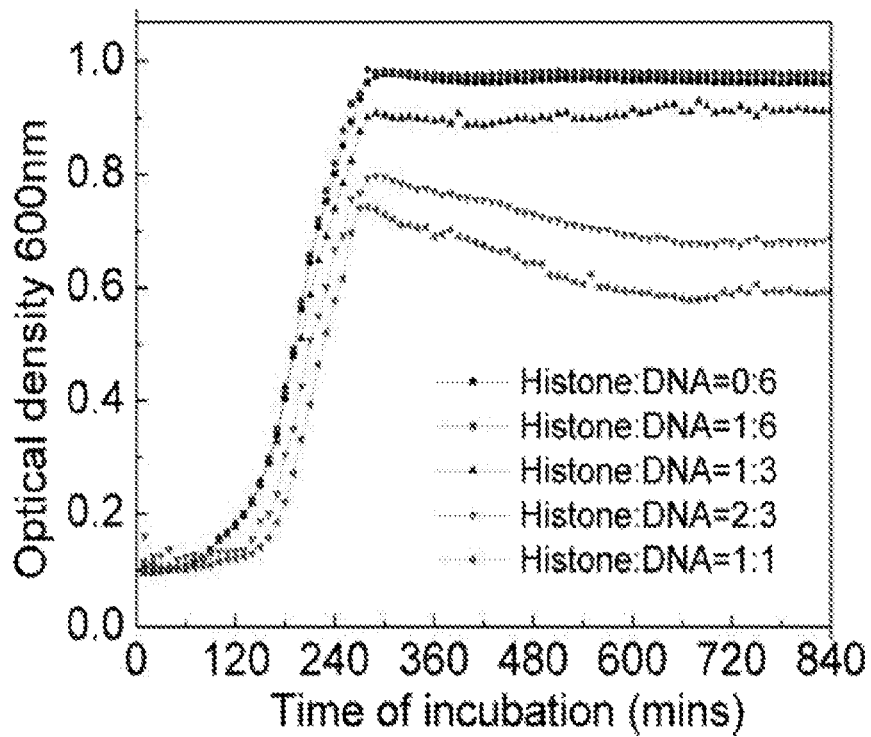
FIG. 16 shows a time dependent growth curve of E. coli after mixing with (a) synthetic NETs prepared with different DNA to histone ratios that did not alter E. coli growth rate significantly but increased the lag time, decreased the final bacteria concentration, and started to show decreases in the optical density at later time points with increasing histone to DNA ratios; (b) solutions of histones alone that decreased bacterial growth rate with increasing concentrations of histone.
Figure 16:
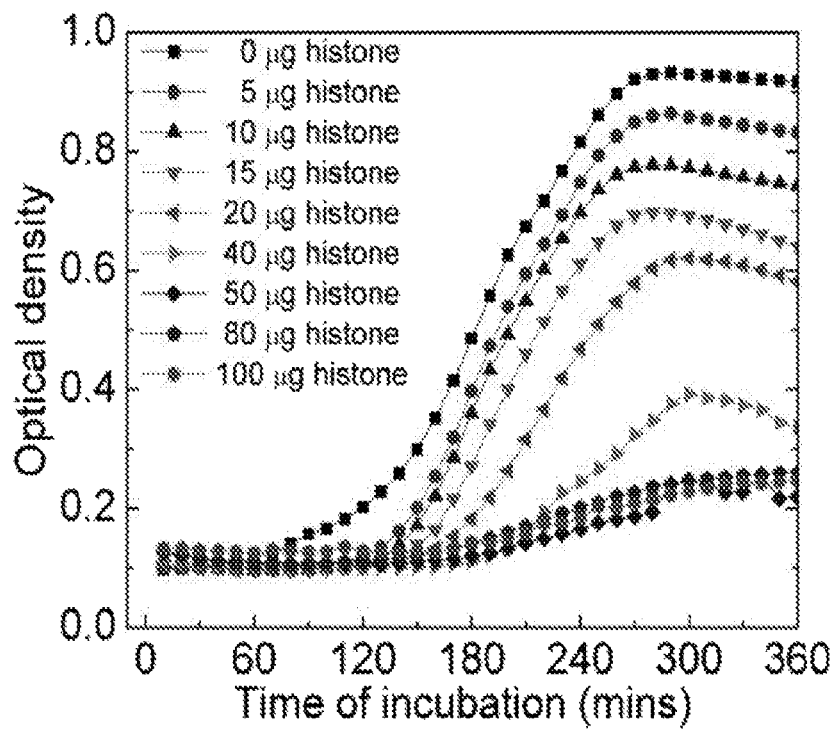

Results are shown in FIG. 16. Histones are a key component of bacteria growth suppression. While DNA alone had no effect on bacteria growth, histone alone did have anti-bacterial effects. Synthetic NETs, which are a complex between DNA and histone, showed more antibacterial activity with increasing proportion of histone compared to DNA. The synthetic NET's anti-bacterial properties may be dependent on release of histones from the synthetic NETs to the bacteria. The positively charged histones should bind the negatively charged bacteria well. This may explain the slow dynamics of bacterial killing by the synthetic NETs.

Synthetic NETs Inhibit Bacteria Growth as Measured by Colony Formation

Quantitative culture quantifies the number of living bacteria at a specific time point by a series of diluting steps and counting the number of colonies that form after culture on agar plate. The general procedure is described below.

1. Suspension of synthetic NETs (40-60 μl) were mixed with one million pathogenic *E. coli* UT189 cells (dispersed in 100 μL TSBG media at an OD value of 0.01 at 600 nm), then 103 units of bovine serum DNase I were added in some samples in an Eppendorf tube and incubated at 37° C. for fixed periods of time (the specific time point varies from 1-6 hrs).
2. 10 μL of the bacteria-NET suspension was diluted stepwise in volumetric ratios of 1:10, 1:102, 1:103, 1:104, 1:105, and 1:106 in a 96 well plate.
3. 10 μL of these suspensions were transferred to an agar plate and the plate incubated at 37° C. for 16 hrs.
4. Finally, the number of colonies of bacteria formed was counted.

Figure 17:
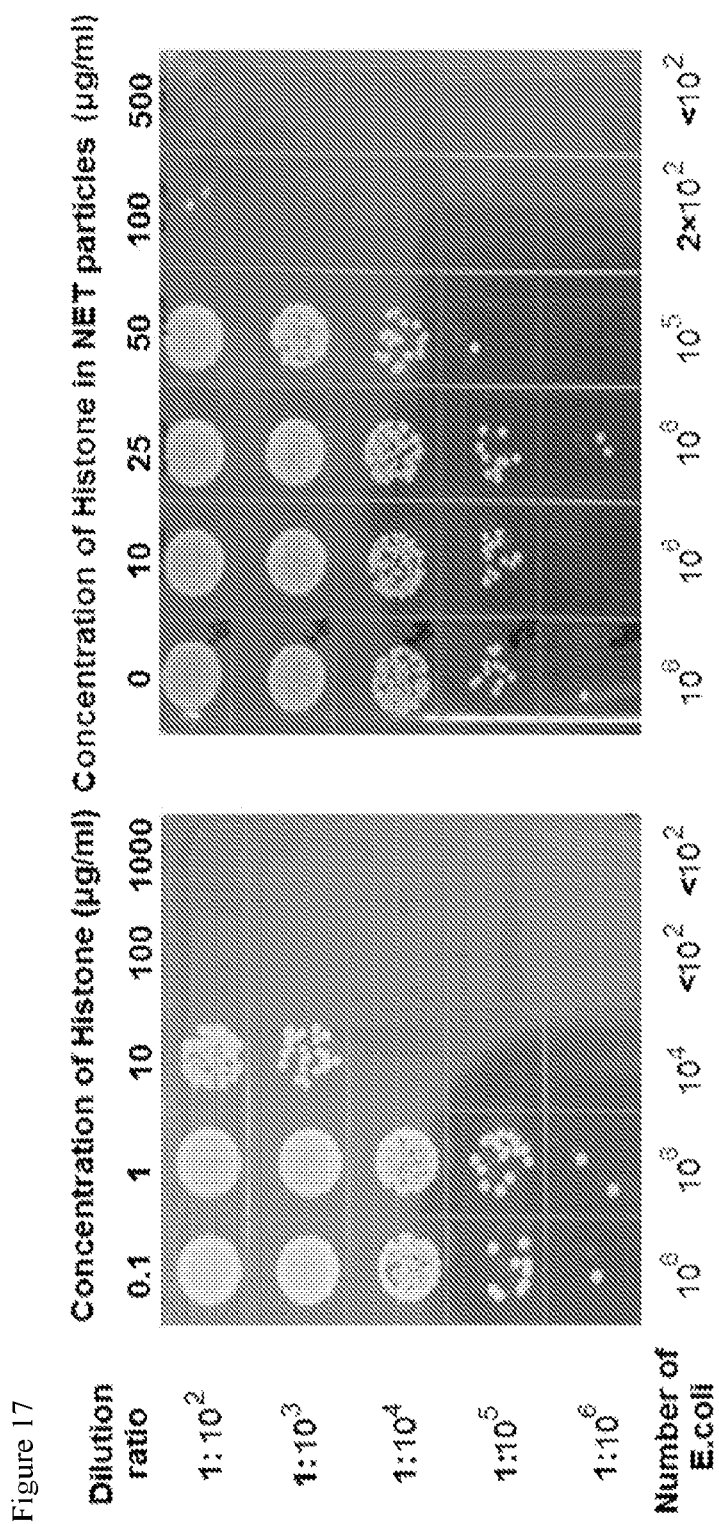
FIG. 17 shows quantitative culture of E. coli after exposure for 1 hr to (a) histone only solution or (b) Bacteria coated with synthetic NETs containing different amounts of histones and additionally treated with DNase.

Results are shown in FIG. 17 and show inhibition of bacterial growth by synthetic NETs.

Synthetic NETs Inhibit Bacteria Growth as Measured by Respiration Rate

In these experiments, bacteria were cultured on synthetic NETs formed on the surface of Seahorse sensor cartridge plates. Sensor cartridges of the XF96 culture plate (@Seahorse) were hydrated in Seahorse XF celebrant solution for 24 hours. This XF96 culture plate was coated with poly-L-Lysine (PLL) by adding 2004 PLL 0.01 wt % to each well and drying at room temperature overnight. 204 DNA/trehalose solution (DNA 1 mg/ml & Trehalose 0.2M) were spotted in each well of the XF96 culture plate and dried overnight under vacuum. 204 histone solutions (with histone concentrations varying from 0, 0.25, 0.5, 0.75, to 1 mg/ml) were dispensed into each well to cover the DNA/trehalose spots. After 2 hours of standing, large synthetic NETs formed inside each well. Carefully removal of the remaining histone solution from the top, was followed by adding 1004 HBSS solution to each well. One million E. coli (in 1004 TSBG culture medium) was added into each well and the culture plate centrifuged at 8000 rpm for 2 mins, so the E. coli settled to the bottom of the culture plate. (The total volume of solution in each well is 2004). These culture plates were covered with the Seahorse sensor cartridge and oxygen consumption rate and extracellular acidification rate measured using the Seahorse extracellular flux analyzer. The respiration of E. coli was followed for 1.5 hours at 37° C.

Figure 18:
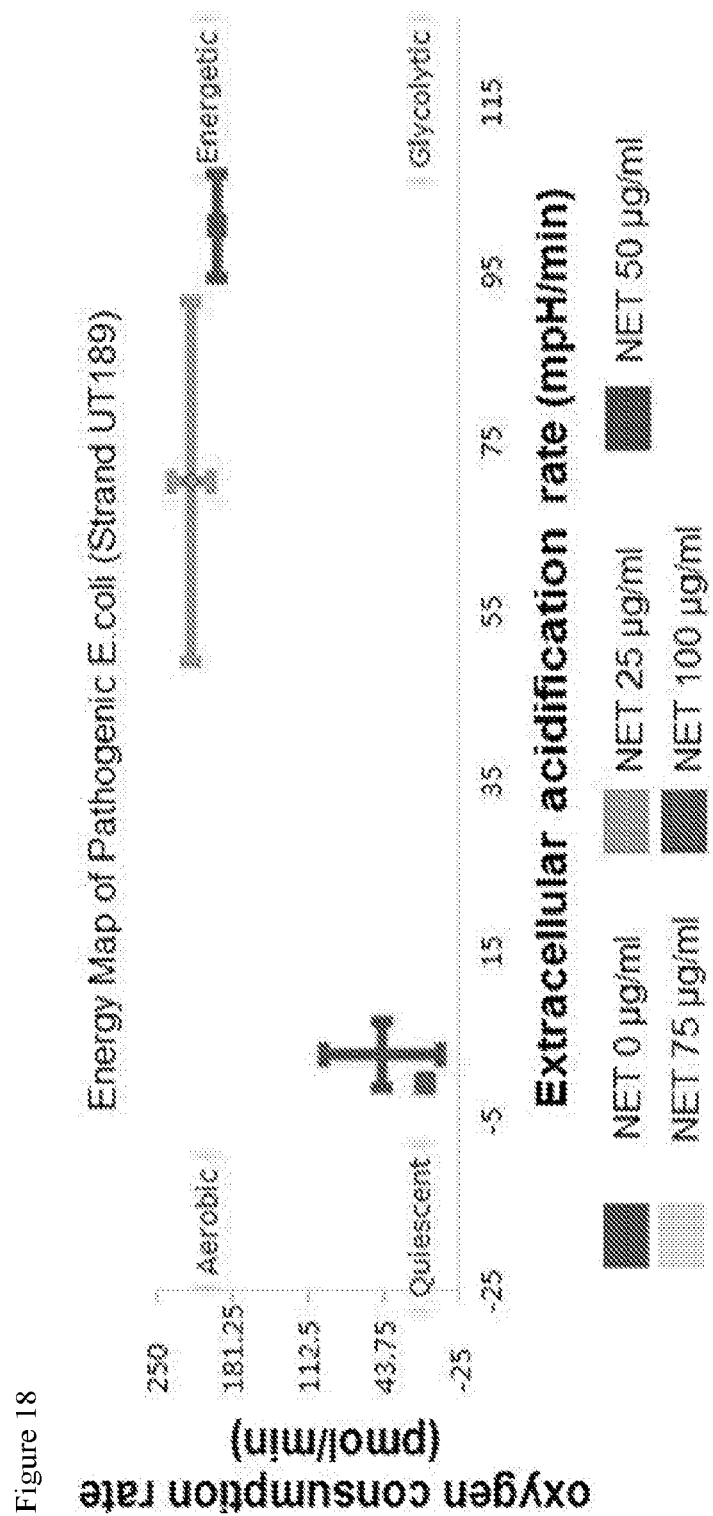
FIG. 18 shows an energy map showing the respiration states of E. coli after incubation with synthetic NETs prepared with different concentrations of histones.

The resultant energy map is shown in FIG. 18. The results show that the synthetic NETs prepared with higher histone concentrations reduce oxygen consumption and acidification by bacteria (promotes quiescent state) supporting an antibacterial effect of the synthetic NETs.

Endothelial Injury

Synthetic NETs Prepared Attached to Floor of Microwell Plates Alter Morphology of Endothelial Cells.

Figure 19:
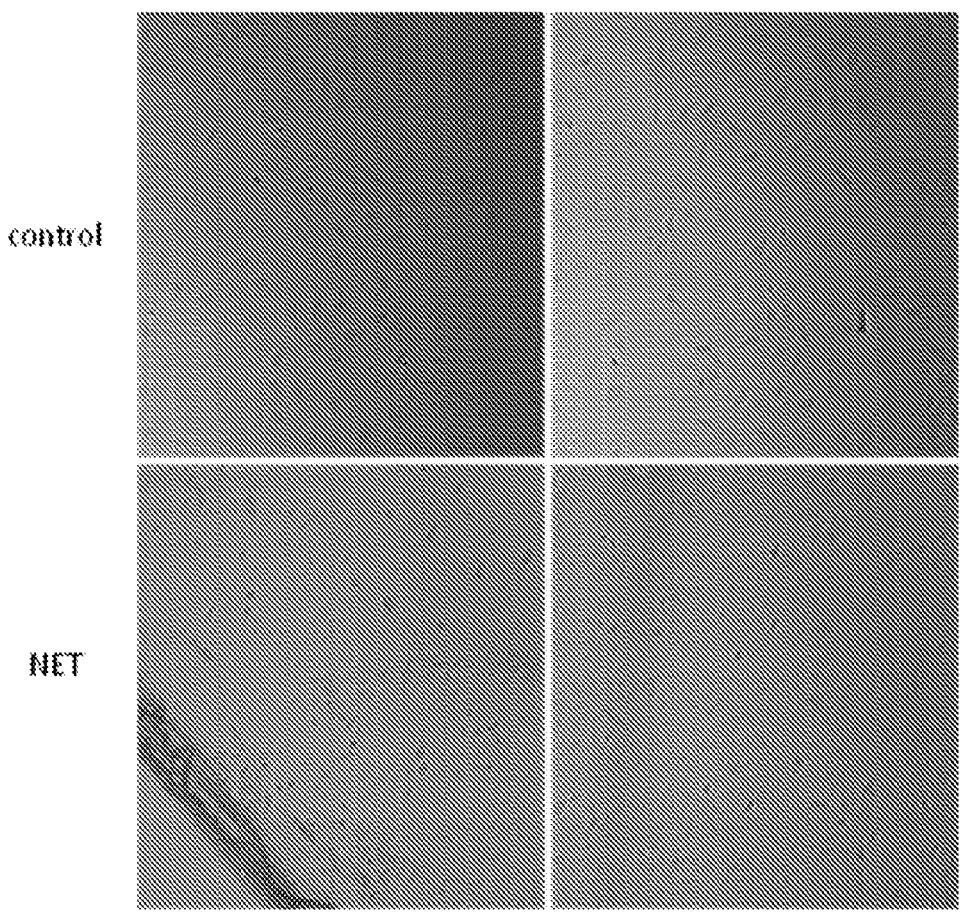
FIG. 19 shows endothelial cells (HUVEC) after 24 hours of culture on synthetic NETs (lower) and in control wells without synthetic NETs (upper).

Synthetic NETs were prepared as described above. Endothelial cells (human umbilical vein endothelial cells (HUVECs)) were seeded in microwells with synthetic NETs or in wells without NETs as controls. They were grown in conventional endothelial cell medium from Lonza. Images show morphological comparisons after 24 hrs. As shown in FIG. 19, the cells on synthetic NETs are not as well spread.

Synthetic NETs Reduce HUVEC Cell Counts and Viability.

Figure 20:
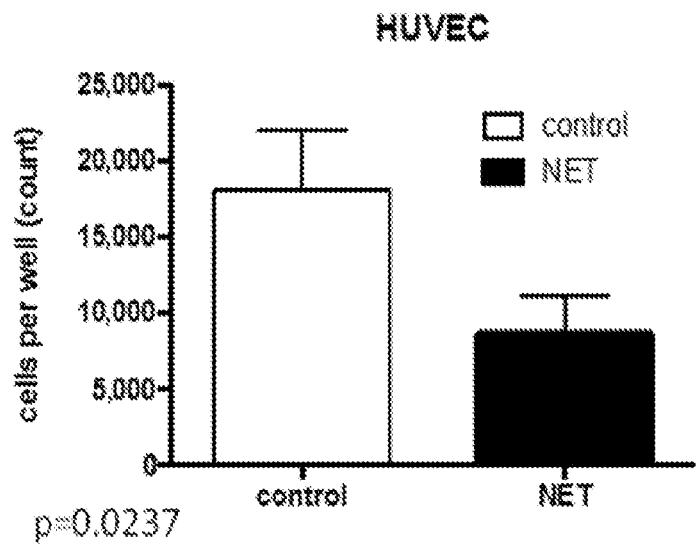
FIG. 20 shows that endothelial cell counts decrease when cultured on synthetic NETs compared to culture in control wells.
Figure 21:
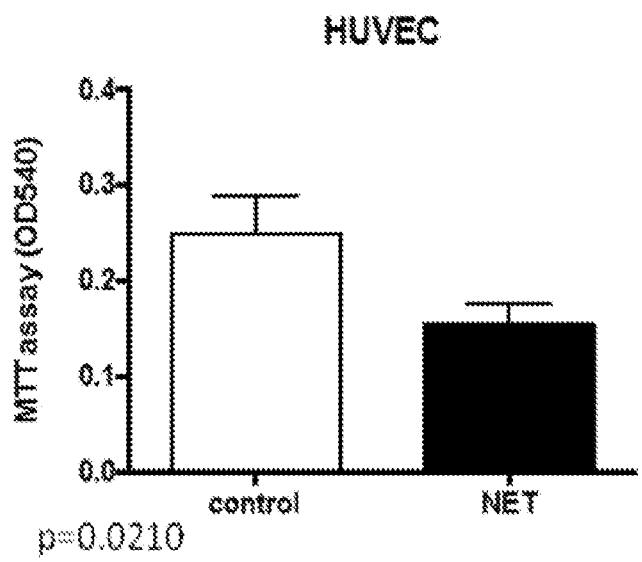
FIG. 21 shows that endothelial cell viability decreases when cultured on synthetic NETs.

Ten thousand HUVECs were plated in 96-well plate with synthetic NETs as described above. After 24 hours of incubation, the cells were detached and counted using trypan blue exclusion method. After 24 hours of incubation, MTT (3-(4,5-dimethylthiazol-2-yl)-2,5-diphenyltetrazolium bromide) dye was added to each well and incubated for 2 hours. After partial removal of the medium, DMSO was added to solubilize formazan. Absorbance at 540 nm was measured. Results are shown in FIGS. 20-21.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are obvious to those skilled in electrical engineering, optics, physics, and molecular biology or related fields are intended to be within the scope of the following claims.

We claim:

1. A system, comprising:
a plurality of in vitro generated three-dimensional structures comprising a network of a polyanion and a polycation, wherein said polyanion is a nucleic acid between approximately 1 kilobase and 1 megabase in length selected from the group consisting of genomic DNA, mitochondrial DNA, bacterial DNA, viral DNA, synthetic DNA, and combinations thereof, wherein said polycation is selected from the group consisting of a histone and a citrullinated histone wherein said structures comprise fibers of said polyanion and said polycation attached to the surface of a solid support; wherein said three-dimensional structures are made by a method, comprising:
dehydrating a first solution comprising a polyanion and an excipient; and
rehydrating said first solution with a second solution comprising a polycation such that said structures are formed.

2. The system of claim 1, wherein said structures are spheres or discs with a diameter of 1 μm to 1 cm.

3. The system of claim 1, wherein each of said fibers, or a bundle of said fibers, is approximately 7-500 nm in diameter and 0.1-100 μm in length.

4. The system of claim 1, wherein said structures are in arrays.

5. The system of claim 1, wherein said structures further comprise a test compound, diagnostic reagent, or therapeutic agent.

6. The system of claim 5, wherein said test compound, diagnostic reagent, or therapeutic agent is selected from the group consisting of a charged compound, a nucleic acid, a cytokine, and a protein.

7. The system of claim 6, wherein said test compound, diagnostic reagent, or therapeutic agent is selected from the group consisting of neutrophil elastase (HNE), LL-37, PAD-4, and Cathepsin-G.

8. The system of claim 1, wherein said structures further comprise a cell or particle.

9. A method of killing or inhibiting the growth of a cell, comprising: contacting the cell with the three-dimensional structures of claim 1.

10. The system of claim 1, wherein said support is selected from the group consisting of a multi-well plate, a particle exterior, a well, a shell, a post, a hydrogel, an elastic surface, a curved surface, a cell, a tissue, a nucleic acid, and a microchannel.

11. The system of claim 1, wherein said system further comprises a test compound, diagnostic biomolecule, or therapeutic agent.

12. The system of claim 11, wherein said test compound, diagnostic biomolecule, or therapeutic agent is selected from the group consisting of a charged compound, a nucleic acid, a cytokine, and a protein.

13. A method, comprising:
a) contacting the composition of claim 1 with a test compound: and b) measuring a change in at least one property of said structure in the presence of the test compound relative to absence of said test compound.

14. The method of claim 13, wherein said test compound is a drug or disease related antibody.

15. The method of claim 13, wherein said property is degradation of said structures or binding of disease biomolecule.

16. A method of screening a sample, comprising:
a) contacting the structures of the composition of claim 1 with a test sample comprising blood or a blood product; and
b) measuring binding of a biomolecule is said sample to said structures.

17. The system of claim 1, wherein said polyanion is genomic DNA and said polycation is a histone.

18. The system of claim 1, wherein said excipient is trehalose or dextran.

19. The method of claim 15, wherein said binding of disease biomolecules are disease-related antibodies.

* * * * *